United States Patent
Wang et al.

(10) Patent No.: US 8,591,865 B2
(45) Date of Patent: *Nov. 26, 2013

(54) RENAL FUNCTION ANALYSIS METHOD AND APPARATUS

(75) Inventors: Exing Wang, Carmel, IN (US); Daniel Meier, Indianapolis, IN (US); Robert Bunch, Terre Haute, IN (US); Bruce Molitoris, Indianapolis, IN (US); Ruben Sandoval, Indianapolis, IN (US); Matthew Rubin, Indianapolis, IN (US); Erinn Sheridan, Indianapolis, IN (US)

(73) Assignee: Pharmacophotonics, Inc., Indianapolis, IN (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/946,471

(22) Filed: Nov. 15, 2010

(65) Prior Publication Data

US 2011/0201940 A1   Aug. 18, 2011

Related U.S. Application Data

(63) Continuation-in-part of application No. 12/425,827, filed on Apr. 17, 2009.

(60) Provisional application No. 61/046,273, filed on Apr. 18, 2008.

(51) Int. Cl.
*A61B 10/00* (2006.01)
*A61B 5/00* (2006.01)
*A61B 8/00* (2006.01)

(52) U.S. Cl.
USPC ........... 424/9.6; 424/1.11; 424/1.65; 424/9.1; 424/9.2

(58) Field of Classification Search
USPC ............ 424/1.11, 1.65, 9.1, 9.6, 9.2; 600/315
See application file for complete search history.

(56) References Cited

U.S. PATENT DOCUMENTS 6,280,703 B1 *   8/2001   Combs et al. .................. 424/9.1
2005/0020891 A1 *   1/2005   Rubinstein et al. ........... 600/315

* cited by examiner

*Primary Examiner* — D L Jones
(74) *Attorney, Agent, or Firm* — Novak Druce Connolly Bove + Quigg LLP

(57) ABSTRACT

A method for measuring a glomerular filtration rate of a mammalian subject comprises a source of reporter and marker fluorescent molecules. The fluorescent molecules are introduced into the vascular system of the mammalian subject. Over a period of time, a measurement of the intensities of the reporter and marker fluorescent molecules is taken. A ratio is calculated to determine the glomerular filtration rate.

5 Claims, 15 Drawing Sheets

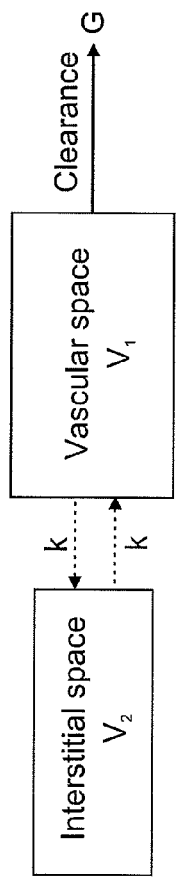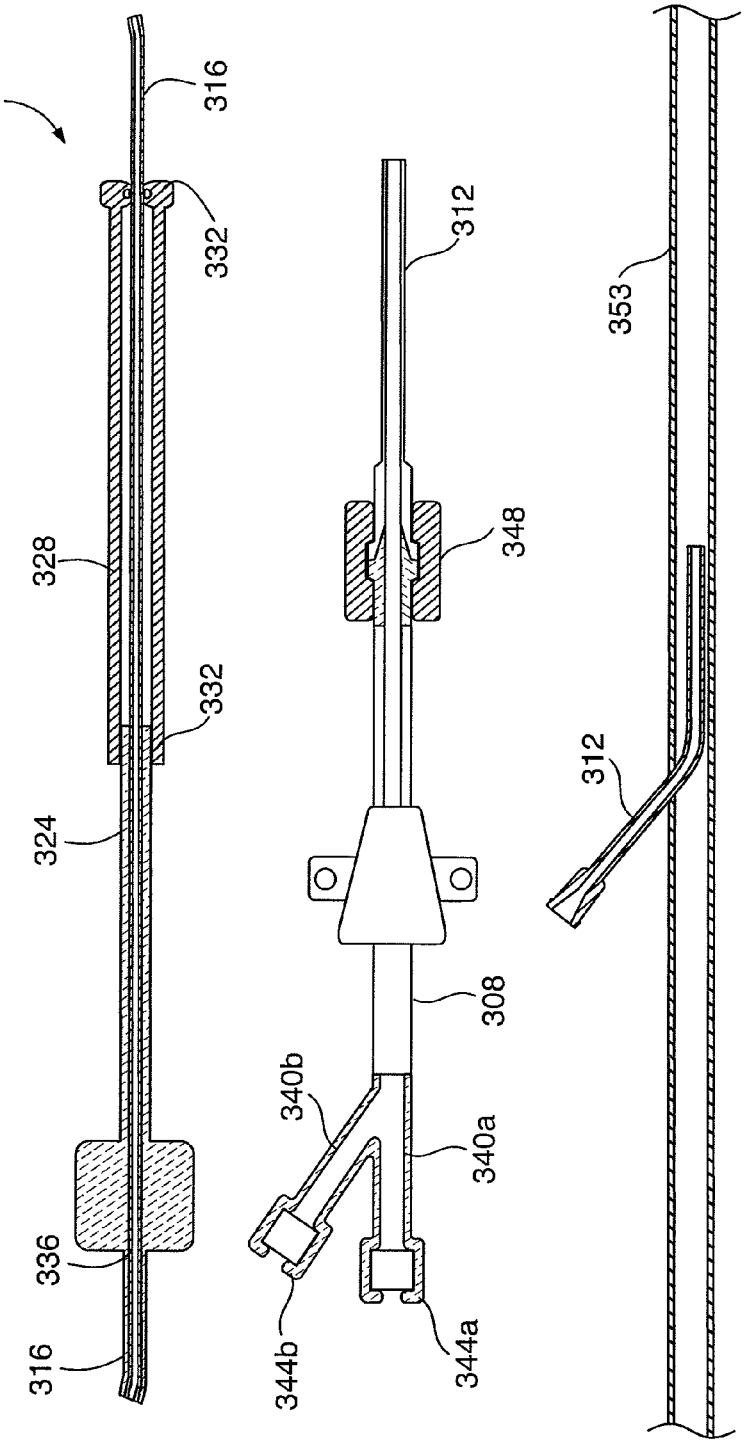
FIG. 15
FIG. 16

RENAL FUNCTION ANALYSIS METHOD AND APPARATUS

CROSS REFERENCE TO RELATED APPLICATIONS

The present application is a continuation-in-part of co-pending U.S. patent application Ser. No. 12/425,827 filed on Apr. 17, 2009, which claims the benefit of U.S. Provisional Patent Application No. 61/046,273, filed on Apr. 18, 2008, the disclosures of which are incorporated by reference as if fully set forth herein.

TECHNICAL FIELD

The invention relates to medical methods and devices used in conjunction with analyzing organ functions of a mammalian subject. More particularly, the present invention is directed to an apparatus and method used for real time measurement of the glomerular filtration rate (GFR) of the kidney in a mammalian subject.

BACKGROUND OF THE INVENTION

Acute kidney injury (AKI) is a serious and deadly disease process affecting 5-10% of all hospitalized patients. The mortality rate in these cases often exceeds 50%. AKI is independently associated with increased mortality rates in several clinical situations, including subsequent to administration of radio contrast dye and cardiovascular surgery. It is often multi-factorial in etiology, especially in critically ill patients. The relative importance of individual factors depends upon the underlying pathology and patient co-morbidities.

Recent data demonstrate an alarming increase in the total number of cases of AKI. Utilizing patient claims in the Medicare 5% sample from 1992-2001, Xue et al (J Am Soc Nephrol 17:1135-1142 2006) have shown that during this time period, the incidence of AKI increased approximately 11.6% per year from 23.6 cases per 1,000 discharges in 1992 to 63.3 cases per 1,000 patients in 2001.

In a recent study, Hsu et al (Hsu, et al., "Community-Based Incidence of Acute Renal Failure," Kidney Int. 2007; 72(2): 208-12.) quantified the incidence of non-dialysis and dialysis AKI among members of a large integrated health care delivery system. Between 1996 and 2003, the incidence of non-dialysis-requiring AKI increased from 323 to 522 while the incidence of dialysis-requiring AKI increased from 20 to 30 per 100,000 person years. Furthermore, hospital death rates were much higher in patients with AKI than in non-AKI discharges. Patients without AKI had a 4.6% in-hospital death rate while those with primary AKI and secondary AKI had rates of 15.2 and 32.6%, respectively. Death within 90 days after hospital admission was 13.1% in discharges without AKI, 34.5% and 48.6% of patients with primary and secondary AKI, respectively. In this large study, the probability of developing end stage renal disease was 18.8% in patients with acute kidney injury as a principle diagnosis and 10.1% in patients with acute renal failure as a secondary diagnostic code. Finally, using the data collected, it was calculated that at least 22.4% of the end stage renal disease (ESRD) cases in the United States come from Medicare beneficiaries who had hospital acquired AKI.

These data are in agreement with observations made by Dr. Paul Eggers, director of epidemiology NIDDK, indicating a rapid increase in the percentage and absolute number of hospitalized patients with AKI as a primary or secondary diagnosis and in patients with chronic kidney disease (CKD) progressing onto ESRD having had AKI as a hospital diagnosis.

In another study (Uchino, et al., "An Assessment of the RIFLE Criteria for Acute Renal Failure in Hospitalized Patients," Crit. Care Med. 2006; 34(7):1913-7.) the incidence and outcomes of 20,126 hospitalized patients was determined in a retrospective single-center study. Of these patients 14.7% required ICU admission, 18% had AKI, and mortality correlated with the extent of kidney injury. Finally, in a multi-center retrospective ICU study AKI occurred in 67% of admissions and again the overall prognosis correlated with the severity of AKI.

Clearly, the prevalence of AKI in hospitalized patients is increasing at an alarming rate. The severity of injury determines hospital outcomes, and AKI accelerates the development of chronic kidney disease and progression of CKD to ESRD.

It is believed that glomerular filtration rate GFR is the most relevant metric for determining the extent of AKI and progression of CKD. Reductions in the GFR secondary to kidney injury, either acute or chronic, are accompanied by increases in blood urea nitrogen (BUN) and serum creatinine levels. Currently, either serum creatinine or an equation based on the serum creatinine is used to determine a patient's estimated GFR (eGFR). Unfortunately, these two approaches are not reliable over the full range of GFR, and neither can be used in AKI, since both muscle mass (creatinine is a breakdown product of creatine, which is an important part of muscle) and GFR determine a patient's serum creatinine level.

Using serum creatinine as an indicator of GFR is highly patient specific. For instance, a serum creatinine of 1.0 mg/dl is indicative of a normal GFR (100 ml/min) in a 70 Kg (154 lb) male with normal muscle mass. However, in a 50 Kg (110 lb) male with moderate muscle wasting, a serum creatinine of 1.0 mg/dl is seen even though his GFR is only 50 ml/min. Formulas derived from large population studies have been developed to factor in patient weight, age, sex and race. However, even these formulas are inaccurate and often misleading in estimating GFR below 20 or above 60 ml/min. Therefore, this is another reason they cannot be used in the setting of AKI.

Recent data indicate that even very small changes in kidney function, as determined by small total equilibrium elevations in serum creatinine, previously felt to be clinically insignificant, are now known to predict an increased mortality rate. Several recent publications have utilized the Risk, Injury, Failure, Loss and ESRD criteria (often called "RIFLE" criteria) to stratify patients into apparent levels of injury based on the maximum serum creatinine obtained and the need for dialysis. Data collected for mortality, length of hospital stay (LOS), LOS of ICU stay, hospital costs, and the need for renal replacement therapy related to the highest stage achieved in this stratification system. These data indicate that the severity or extent of kidney injury in AKI is an important prognostic indicator of a patient's outcome. Furthermore, early changes in organ function predict survival in severe sepsis. 100121 Serum creatinine determinations as a measure of GFR may also be severely limiting because of the time it takes to reach equilibrium values required for an accurate conversion. Patients with acute renal failure develop an abrupt decline of their GFR; however, the magnitude of this decline is only apparent after several days of equilibration if determined by a rising serum creatinine. For instance, if a patient was to lose 95% of his GFR secondary to AKI, the GFR would decrease from 100 to 5 ml/min rapidly, but the serum creatinine would only rise by 1 mg/dl/day. This slow rise in serum creatinine limits the physician's ability to diagnose the injury for 12-24 hours after the event, and it is also not possible to determine the extent of injury for days. This has markedly limited the ability to conduct a therapeutic trial in AKI. Since the extent of the decline in GFR, or eventual plateau in serum creatinine, correlates with morbidity, mortality and recovery potential, the ability to accurately determine GFR in patients with acute kidney injury is of great clinical importance for rapid diagnosis, stratification and timely treatment.

It is widely held that beginning therapy after 12-24 hours of AKI may limit the success rate of any potential therapeutic agent. Therefore, a search for a biomarker of kidney injury has intensified and is now considered by many experts to be the highest priority in the field of AKI. Potential molecules include NGAL, KIM-1, IL-18, and several others. Any one biomarker, or probably a combination of biomarkers, will serve as structural markers of injury. However, improvements sought utilizing these structural biomarkers may not be significant because they were developed using population results that may not apply to an individual.

Collection of a 24 hour urine and invasive techniques exist to accurately determine a patient's GFR, but these are cumbersome, error prone, expensive, time consuming, or expose the patient to radiation or radio contrast media. Also, there is no rapid and accurate measurement technique that can determine GFR reliably in patients with acute kidney injury when the serum creatinine is rising.

The present invention is provided to solve the problems discussed above and other problems, and to provide advantages and aspects not provided by prior diagnostic techniques. A full discussion of the features and advantages of the present invention is deferred to the following detailed description, which proceeds with reference to the accompanying drawings.

SUMMARY OF THE INVENTION

One aspect of the present invention is directed to a composition for introduction into a mammalian subject's vascular system to measure the Glomerular Filtration Rate (GFR) of the mammalian subject. The composition comprises a reporter molecule and a marker molecule. The reporter molecule should be filtered by the kidney, which may be determined by the reporter molecule having a glomerular sieving coefficient (GSC) of from about 0.5 to about 1.0, preferably from about 0.7 to about 1.0, and more preferably from about 0.9 to about 1.0, while the marker molecule should be retained in the vascular system, which may be determined by the marker molecule having a GSC of about 0.0 to about 0.5, preferably from about 0.0 to about 0.2, wherein the GSC of the reporter molecule is greater than the GSC of the marker molecule by at least 0.4. In a preferred embodiment, the GSC of the reporter molecule is greater than the GSC of the marker molecule by at least 0.6. In a more preferred embodiment, the GSC of the reporter molecule is greater than the GSC of the marker molecule by at least 0.8. The reporter molecule and the marker molecule should be chemically stable in the vascular system during the measurement of the GFR.

The reporter molecule may have a first fluorescent characteristic, and the marker molecule may have a second fluorescent characteristic. These fluorescent characteristics may not be equal, e.g. having differing wavelengths. The first fluorescent characteristic may be a first fluorescence excitation wavelength and a first fluorescence emission wavelength. The second fluorescent characteristic may be a second fluorescence excitation wavelength and a second fluorescence emission wavelength. The first and second fluorescence excitation wavelengths and the first and second fluorescence emission wavelengths may be different, unequal, or distinguishable.

The reporter molecule and the marker molecule may share a common molecular property. The reporter molecule has a reporter molecule molecular property of a first quality, and the marker molecule has a marker molecule molecular property of a second quality which is distinguishable from the reporter molecule molecular property first quality. The molecular property may be chosen from the group consisting of molecular weights, molecular sizes, molecular shapes, molecular charges, and binding to serum protein.

When the molecular property is molecular weight, the reporter molecule may have a first molecular weight and the marker molecule may have a second molecular weight. The first molecular weight may be less than the second molecular weight, and may be substantially less. The first molecular weight may be of a magnitude wherein the reporter molecule is filtered by a properly functioning mammalian kidney. The second molecular weight may be great enough to resist filtration of the marker molecule by a mammalian kidney. Optionally, the first molecular weight may be of a magnitude wherein the reporter molecule is readily filtered by a properly functioning mammalian kidney, while at the same time, the second molecular weight is great enough to resist filtration of the marker molecule by a mammalian kidney. The first molecular weight may be chosen from a group of a range from about 0.5 kD to about 50 kD. The second molecular weight may be chosen from a group above about 100 kD.

When the molecular property is binding to serum protein, the reporter molecule may not bind to serum protein and the marker molecule may bind to serum protein.

The reporter and marker molecules may be dextrans.

The reporter molecule or the marker molecule may comprise a fluorescein. The fluorescein may be conjugated to a macromolecule such as, but is not limited to, polymer, protein, dextran, cellulose, carbohydrate, lipid or nucleic acid.

The reporter molecule or the marker molecule may be amino fluorescein dextran.

The reporter molecule or the marker molecule may be fluorescein isothiocyanate-inulin (FTIC-inulin).

Alternatively, the reporter molecule or the marker molecule may comprise a rhodamine dye. The rhodamine dye may be conjugated to a macromolecule such as, but is not limited to, polymer, protein, dextran, cellulose, carbohydrate, lipid or nucleic acid.

The reporter molecule or the marker molecule may be a sulforhodamine 101 dextran.

In an embodiment, the reporter molecule comprises a fluorescein conjugated with a macromolecule and the marker molecule comprises a rhodamine dye conjugated with a macromolecule.

A second aspect of the present invention is directed to a system for measuring fluorescence intensity of a fluorescent molecule in the vascular system of a mammalian subject. The system comprises a source of a fluorescent molecule, a means for introducing the fluorescent molecule into a vascular system of the mammalian subject, a means for measuring the fluorescence intensity of the fluorescent molecule within the vascular system, and a means for reporting the measured fluorescence intensity of fluorescent molecule within the vascular system. The means for introducing may include a catheter. The means for measuring may include an optic fiber in communication with a detector. The means for reporting may include determining an intensity ratio between two or more fluorescent molecules measured within the vascular system. The source of fluorescent molecules may comprise a plurality of fluorescently conjugated molecules. The system may further have a means to calculate the Glomerular Filtration Rate (GFR) of the mammalian subject from the intensity ratio of the fluorescent molecules.

A third aspect of the present invention is directed to a system for measuring fluorescence intensity of a first fluorescent molecule in the vascular system of a mammalian subject. The system comprises an optical means providing a first excitation wavelength to a first fluorescent molecule in the vascular system in the mammalian subject and a means for measuring an emission from the first fluorescent molecule in the vascular system of the mammalian subject in response to the first excitation wavelength.

The optical means may provide a second excitation wavelength to a second fluorescent molecule in the vascular system of the mammalian subject, and the system may further comprise a means for measuring an emission from the second fluorescent molecule in the vascular system of the mammalian subject in response to the second excitation wavelength.

The system of the third aspect of the invention may further comprise a means for calculating a ratio of the emission from the first fluorescent molecule to the emission from the second fluorescent molecule. The system may still further comprise a means for reporting the ratio.

A fourth aspect of the present invention is directed to an optical apparatus for measuring a first intensity of a first emitted fluorescence signal of a first fluorescent molecule within a vascular system of a mammalian subject. The apparatus comprises a source of a first fluorescent excitation wavelength, a delivery optical path along which the first fluorescent excitation wavelength passes, an excitation site to which the first fluorescent excitation wavelength is delivered, a return optical path along which a first emitted fluorescence signal passes, and a means for detecting an intensity of the first emitted fluorescence signal. This apparatus may further comprise a source of a second fluorescent molecule having a second fluorescence excitation wavelength and a second fluorescence emission wavelength.

The means for detecting may be chosen from a group consisting of a photo multiplier tube, a photo detector, a solid state detector, and a charge-coupled device.

The excitation site may include a fiber optic cable.

A fifth aspect of the invention is directed to an optical apparatus for measuring a relative fluorescence intensity of a first fluorescent molecule within a vascular system of a mammalian subject. The optical apparatus comprises a source of a first fluorescent excitation wavelength, a source of a second fluorescent excitation wavelength, a delivery optical path to the vascular system along which the first and second fluorescent excitation wavelengths pass, an excitation site in the vascular system to which the first and second fluorescent excitation wavelengths are delivered, a return optical path from the vascular system along which a first emitted fluorescence signal and a second emitted fluorescence signal pass from the excitation site, a first means for detecting an intensity of the first emitted fluorescence signal; and a second means for detecting an intensity of the second emitted fluorescence signal.

A sixth aspect of the present invention is directed to a light transfer probe for use in measuring a fluorescence intensity of a fluorescent molecule in the vascular system of a mammalian subject. The light transfer probe comprises a tubular main member having a proximal end opposite a distal end and defining a passageway and a fiber optic cable extending from said proximal end to the distal end within the passageway and extensible from the distal end into free blood flow in the vascular system. The light transfer probe may further comprise an introducer connected to the tubular member at one end and having an opposite end insertable into a vascular system, and/or an insertion tool. A length of the fiber optic cable may be fluid sealed within the insertion tool. The insertion tool may include a first tubular member slidable within a second tubular member. The fiber optic cable may be held captive by a portion of the first tubular member. The insertion tool may be joined to a port of the tubular main member wherein the fiber optic cable passes through the insertion tool and into the tubular main member. The tubular main member may be joined to the introducer by a connector. The fiber optic cable may be extensible from the introducer upon relative movement between the first and second tubular members.

The first and second tubular members may be fluidly sealed.

The fiber optic cable may include a bend on a distal end insertable into a vascular system.

A seventh aspect of the present invention is directed to a light transfer probe for use in measuring a relative intensity of a plurality of fluorescent molecules in the vascular system of a mammalian subject. The light transfer probe comprises a fiber optic cable, a fiber optic insertion tool about a length of the fiber optic cable having a first tubular member sealed to a second tubular member and capable of relative movement therewith, the fiber optic cable held attached to a portion of the first tubular member such that movement by the first tubular member transfers movement to the fiber optic cable, and a tubular main body sealed to the insertion tool, the fiber optic cable passing through a passageway in the tubular main body and extensible therefrom upon relative movement between the first and second tubular members.

The light transfer probe may further comprise an introducer connected to the tubular main body. The introducer is insertable within a vascular system, and the fiber optic cable extensible therefrom.

The fiber optic cable may have a bend at one end. The one end is insertable within a vascular system.

An eighth aspect of the present invention is directed to a method of measuring a glomerular filtration rate in a mammalian subject. This method comprises: (1) providing a known quantity of a fluorescent reporter molecule and a known quantity of a fluorescent marker molecules wherein the fluorescent reporter molecule is filtered by the kidney of the mammalian subject and the fluorescent marker molecule is retained in the vascular system of the mammalian subject, and wherein the fluorescent reporter molecule and the fluorescent marker molecule are chemically stable in the vascular system during the measurement of the GFR and wherein the fluorescent reporter molecule has a first fluorescence excitation wavelength to generate a first fluorescence emission signal having a first fluorescence emission wavelength and the fluorescent marker molecule has a second fluorescence excitation wavelength to generate a second fluorescence emission signal having a second fluorescence emission wavelength, and wherein the first fluorescence emission wavelength is distinguishable from the second emission wavelength; (2) introducing by bolus injection said fluorescent reporter molecule and said fluorescent marker molecule into a vascular system of the mammalian subject; (3) exciting said fluorescent reporter molecule in the vascular system with a first fluorescence excitation wavelength continuously over a period of time for measuring the GFR to generate a series of first fluorescence emission signals having a first fluorescence emission wavelength and exciting said fluorescent marker molecule in the vascular system with a second fluorescence excitation wavelength continuously over the same period of time for measuring the GFR to generate a series of second fluorescence emission signals having a second fluorescence emission wavelength; (4) measuring an intensity of said first fluorescence emission signal and an intensity of said second fluorescence emission signal subsequent to said introducing step and calculating a ratio of the intensity of said first fluorescence emission signal to the intensity of said second fluorescence emission signal wherein said measuring and calculating steps are performed at predetermined intervals and reported in at least substantially real time; (5) obtaining constants $A_2$, $B_2$, $\alpha$, and $\beta$ by fitting the ratio data to the following equation:

$$R(t) = A_2 e^{\alpha t} + B_2 e^{-\beta t}$$

where R(t) is the fluorescence ratio, as a function of time, of the intensity of said first fluorescence emission signal to the intensity of said second fluorescence emission signal, $A_2$ and $B_2$ are constants; $\alpha$ is a fast phase decay constant; and $\beta$ is a slow phase decay constant; and (6) calculating the GFR using the following equation:

$$GFR = \frac{V_1(A_2 + B_2)}{A_2/\alpha + B_2/\beta}$$

wherein $V_1$ is plasma volume.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 15 is a block diagram of a two compartment model;

FIG. 16 is an illustration of a dissembled light transfer probe having an optical fiber.

DETAILED DESCRIPTION

Figure 1:
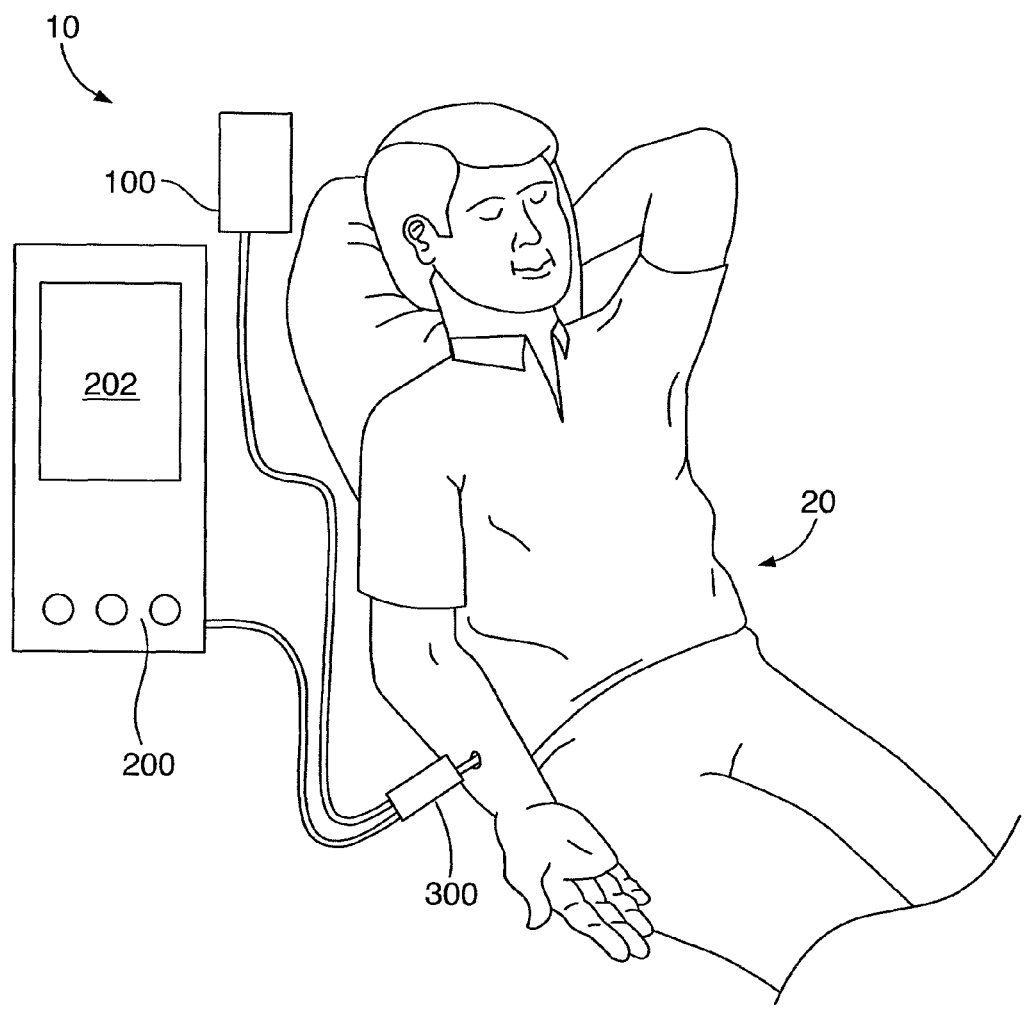
FIG. 1 is an illustration of a system of the present invention utilizing a method of the present invention.

While this invention is susceptible of embodiments in many different forms, there are shown in the drawings and will herein be described in detail preferred embodiments of the invention with the understanding that the present disclosures are to be considered as exemplifications of the principles of the invention and are not intended to limit the broad aspect of the invention to the embodiments illustrated.

The inventors have found that a combination of both structural and functional markers of AKI presents a high level of clinical utility in diagnosing kidney function and kidney-related diseases. Thus, one objective of the present invention is to provide tests for analyzing and quantifying organ function and physiological parameters that have been difficult or impossible to measure in the past. The present invention focuses on a method and device for rapid and substantially real time measurement of Glomerular Filtration Rate (GFR) which can lead to the detection of acute kidney injury and chronic kidney-related diseases in a mammalian subject, preferably a human subject. This development utilizes technology developed by and licensed from the Indiana Center for Biological Microscopy. Such technology is described in U.S.

Provisional Patent Application No. 60/672,708, PCT Application No. US2006/014576, published as WO/2006/113724, and U.S. application Ser. No. 11/911,895, which are hereby incorporated by reference as if fully set forth herein. Specifically, figures of the apparatuses shown in FIGS. 6-9 of WO/2006/113724 and the descriptions of same at the paragraphs numbered 96 to 104 are directed to the technology utilized.

In early animal studies, this technology has proven efficacious in providing accurate and rapid measurement of the true Glomerular Filtration Rate (GFR)—the rate by which the kidney is able to filter waste products from the blood stream. While the need for disease diagnostics varies according to the specific disease, in kidney disease, GFR is the primary clinical indicator of injury, disease progression, or recovery.

GFR measures the amount of plasma filtered through glomeruli within a given period of time. It is clinically the most widely used indicator of kidney function. Physicians routinely use it for both diagnostic and therapeutic decisions. In fact, the National Kidney Foundation has now divided chronic kidney disease patients into five groups (I-V) based upon their estimated GFR (eGFR). This has assisted clinicians in recognizing and understanding the severity of the kidney disease in patients. It has also allowed for the initiation of appropriate therapies based on the patient's baseline GFR.

A variety of techniques such as radioactive and non-radioactive contrast agents, as well as radiographic renal imaging, can measure GFR rapidly. Plasma clearance techniques are based on measuring the plasma clearance of GFR marker molecules. By using radioactive markers, such as $^{51}$Cr-EDTA or [99]m Tc-DTPA ([99]m Technetium diethylene triamine pentaacetic acid), it has been reported that plasma clearance and GFR could both be determined independently using a radiation detector. Using radioactive GFR markers, such as $^{51}$Cr-EDTA and [99]mTc-DTPA ([99]m-Technetium diethylene triamine pentaacetate), in conjunction with a radiation detector, one can monitor GFR in patients with acute kidney injury at rates close to real-time. The measured plasma clearance shows excellent correlations with GFRs simultaneously measured using the standard method with urine collection. However, the use of radioactive GFR markers and the clinical difficulties in administering this test make this method unattractive. By using a fluorescent GFR marker, such as FITC-inulin, with a bolus intravenous infusion followed with drawing blood samples at multiple time points, one can accurately determine GFR. Potentially, with the development of a suitable contrast agent, magnetic resonance imaging (MRI) techniques can be very useful for providing kidney functional diagnostics. The downside of using such technologies is the low accessibility, associated high cost, difficulty repeating the study and the need to move the patient for the study.

Similarly, the plasma concentration of non-radioactive markers, e.g. iothalamate, determined by standard methods, such as high-performance liquid chromatography (HPLC), has also been used to evaluate renal function in critically ill patients. Such plasma clearance based GFR measurement techniques have been reported to have good time resolution in detecting changes of renal function in patients with severely impaired renal function. By using bolus infusion of a single fluorescent GFR marker, FITC-inulin, GFR has been determined by sequentially measuring the fluorescence signals in the blood samples drawn as a function of time after infusion. The inventors have expanded upon and enhanced this approach offering improved accuracy, rate of determination, and reduced exposure to potentially toxic radioactive molecules.

Inulin, a small fructose polymer that is filtered, and cleared from the body only by glomerular filtration, is a reference standard GFR marker. Other non-radioactive markers (such as iothalamate, iohexol, polyfructosan) and radioactive ones (such as $^{125}$I-iothalamate and $^{51}$Cr-EDTA) are also commonly used.

In clinical practice, endogenous markers such as serum creatinine and cystatin C are routinely used to estimate GFR, since the production and tubular reabsorption rates of these molecules vary significantly from different individuals. Cystatin C has received recent attention as a superior endogenous serum marker of GFR, compared to serum creatinine, as it is elevated up to a day earlier than creatinine in an ICU population with AKI.

The inventors have developed a minimally invasive device for direct measurement of GFR in mammalian subjects, such as humans, using a multi-photon microscopy method, preferably a two photon microscopy method. The method relies on reading two fluorescent molecules attached to different size dextran molecules. Dextran is a complex, branched polysaccharide made of many glucose molecules joined into chains of varying lengths (from 3 to 2,000 kD). Thus, another objective of the present invention is to provide both a method and apparatus using a catheter based light transfer probe to read the fluorescent markers. This light transfer probe can be placed into a vascular system, e.g., an arm vein of a mammalian patient, to allow the concentration of fluorescent markers to be monitored in real time, providing a direct measurement of GFR.

A rapid and accurate measurement of GFR in an early stage of acute kidney injury is important for diagnosis, stratification of extent of injury and therapeutic purposes. An advantage of the present invention is that it will rapidly identify and determine the extent of injury allowing for early treatment, including dialysis initiation, as well as enrollment and stratification for clinical studies. It could also be used to determine the effect of a clinical maneuver on GFR, such as volume resuscitation. Therefore, this technical advance is of major clinical importance, especially in high risk patients where intense surveillance is necessary for early diagnosis, injury stratification and determination of therapeutic potential.

The inadequacies of methods currently clinically used for estimating GFR are established both in literature and in practice. While progress is being made to identify biomarkers for detecting presence of injury, little progress has been made in finding a functional marker that is practical enough for broad acceptance. The inventors' method represents a true advancement in the ability to accurately quantify and track the degree of kidney function with near real-time efficiency. The inventors have also developed a device that is easy to operate in a busy medical environment—a critical adoption barrier in medical technology.

The optical technique developed by the inventors is based on plasma clearance measurements of a fluorescent bioreporter molecule and allows for the rapid, frequent, and safe evaluation of GFR. To further validate the values, other standard GFR tests, including but not limited to inulin clearance, may be performed. Upon comparison of these values, a correction factor may be applied to the data obtained using this novel method if needed.

Referring to FIG. 1, a system 10 which incorporates a method of the present invention is illustrated. The system 10 comprises a source of a GFR measurement composition 100, a kidney fluorescent detector 200, and a light transfer probe 300. The GFR measurement composition 100, which comprises a plurality of reporter molecules and a plurality of marker molecules, is introduced into the blood stream of a human subject 20 via the light transfer probe 300. The fluorescent detector 200 includes a light source to provide one or more exciting lights which travel from the detector 200 to the blood stream via the light transfer probe 300 to excite the GFR measurement composition 100 in the blood stream of the subject. The fluorescent detector 200 monitors the level of the GFR measurement composition within the blood stream and reports an operating condition of the human subject's kidney in at least substantially real time. This apparatus measures volume of plasma distribution based on a fluorescence of a marker molecule relative to the fluorescence of a reporter molecule. "Substantially real time" is intended to encompass the duration elapsed between measurement of the levels of the reporter and the marker within the blood stream, calculation of the operating condition of the kidney, and reporting of that condition. It is contemplated by the inventors that this elapsed time will be very near real time as to be negligible in relation to the prior techniques discussed above.

The GFR Measurement Composition

By utilizing intravital multi-photon microscopic imaging of the kidney, the inventors have quantified glomerular filtration and tubular reabsorption processes independent of each other. The inventors have developed ratiometric imaging techniques permitting quantitative analysis of fluorescence signals within local regions of the kidney using multi-fluorescent probe experiments. To measure GFR by plasma clearance, the inventors use a fluorescent GFR reporter molecule, e.g. fluorescein isothiocyanate (FITC) dextran, together with a large different fluorescent marker molecule that does not pass through the glomerular filtration barrier. This large fluorescent marker serves to quantify the plasma volume of distribution in the vascular space and allow for the ratiometric technique.

The inventors have been able to quantify plasma clearance of the fluorescent GFR marker by examining the ratio of fluorescence intensities of the two molecules from within the blood vessel regions of the image. GFR can be rapidly determined using this ratio technique. This method has been tested in a number of animal models. Since the fluorescent signals are being measured from within the blood vessels to quantify the kinetics of plasma clearance, the ratio signal of the two fluorescent molecules is independent of the body location where the measurement is performed.

To measure GFR accurately, the inventors have determined that the ideal GFR reporter molecule and marker molecule should both be chemically stable within the vascular system during the study. What is meant by "chemically stable within the vascular system" is that the molecules are not notably metabolized during the study. The reporter molecule should be filtered by the kidney of the mammalian subject while marker molecule should be retained in the vascular system of the mammalian subject. What is meant by "retained within the vascular system" means that the marker molecule is retained in the vascular space of the vascular system, does not distribute, or substantially distribute, into the interstitial space and the molecule should not be, or should substantially not be, secreted, reabsorbed, or filtered within the kidney. Whether the reporter molecule is filtered by the kidney or retained in the vascular system may be determined by the value of its glomerular sieving coefficient (GSC). The reporter molecule should have a GSC value of from about 0.5 to about 1.0, preferably from about 0.7 to about 1.0, and more preferably from about 0.9 to 1.0. The marker molecule should have a GSC value of from about 0.0 to about 0.5, preferably from 0.0 to about 0.2. The GSC value of the reporter molecule should be greater than that of the marker molecule by at least 0.4, preferably 0.6 and more preferably 0.8. "Substantially" or "about" as used here is limited to ±5%. Satisfying these conditions, the GFR would be equal to the urinary clearance of the reporter after its intravenous infusion.

GSC of a molecule can be determined by any one of the known methods. One of such method is disclosed by Russo et al. (Russo, L M, Sandoval, R M, McKee, M, Osicka, T M, Collins, A B, Brown, D, Molitoris, B A and Compter, W D; "The Normal Kidney Filters Nephrotic Levels of Albumin Retrieved by Proximal Tubule Cells: Retrieval is Disrupted in Nephrotic States"; Kidney Int. 71:504-513, 2007; also published in Kidney Int. Advanced Online Publication 17 Jan. 2007).

There are many molecular properties which may determine whether a molecule is filtered by the kidney, and therefore can be used as a reporter molecule for the measurement of GFR or a molecule is retained in the vasculature, and therefore can be used as a marker molecule. Some of the properties include, but are not limited to, molecular weight, size, shape, charge or binding to serum protein. For example, molecules smaller in size or with lower molecular weights are more likely to be filtered by the kidney and molecules larger in size or higher in molecular weights are more likely retained in the vasculature. Similarly, rounded molecules are more likely to be filtered by the kidney and elongated molecules are likely to be retained in the vasculature. Neutral of negatively charged molecules are likely to be filtered by the kidney and positively charged molecules are likely to be retained in the vasculature. Molecules not bound to serum protein are likely to be filtered by the kidney and molecules bound to serum protein are likely to be retained within the vasculature.

One aspect of the present invention is directed to a composition for introduction into a mammalian subject's vascular system to measure the GFR of the mammalian subject. The composition comprises a reporter molecule and a marker molecule as described above. The reporter molecule and the marker molecule of the composition may share a molecular property. The molecular property may be selected from the group consisting of molecular weights, sizes, shapes, charges and binding to serum protein. The reporter molecule has a first quality of the molecular property, and the marker molecule has a second quality of the molecular property wherein the first quality is distinguishable from the second quality.

One of the molecular properties is molecular weight. The molecular weight of the reporter molecule may be less than that of the marker molecule. Preferably, the molecular weight of the reporter molecule is from about 0.5 kD to about 50 kD and that of the marker molecule is greater than about 100 kD.

Yet another molecular property is binding to serum protein, wherein the reporter molecule does not bind to serum protein while the marker molecule binds to serum protein.

In another aspect of the present invention, the reporter molecule has a first fluorescent characteristic and the marker molecule has a second fluorescent characteristic. The first fluorescent characteristic and the second fluorescent characteristic may be distinguishable. The first fluorescent characteristic may be a first fluorescence excitation wavelength and a first fluorescence emission wavelength, and the second fluorescent characteristic is a second fluorescence excitation wavelength and a second fluorescent emission wavelength. The first and second fluorescence excitation wavelength and the first and second fluorescence emission wavelengths may be unequal.

In one embodiment, the reporter and/or marker molecule may be a dextran.

In another embodiment, the reporter molecule or the marker molecule may comprise a fluorescien. The fluorescien may be conjugated to a macromolecule, such as, but is not limited to, polymer, protein, dextran, cellulose, carbohydrate, lipid or nucleic acid. An example of such a molecule is fluorescein dextran. Another example is amino fluorescein dextran. A further example is fluorescein isothiocyanate-inulin (FITC-inulin).

In another embodiment, the reporter molecule or the marker molecule may comprise a rhodamine dye, such as, but not limited to, sulforhodamine dye. The rhodamine dye may be conjugated to a macromolecule, such as, but is not limited to, polymer, protein, dextran, cellulose, carbohydrate, lipid or nucleic acid. An example of a sulforhodamine dye is sulforhodamine 101 (Texas Red®) dextran. Additional rhodamine dyes suitable for the present invention are disclosed in United Provisional Patent Application No. 61/320,571, which is hereby incorporated by reference as if fully set forth herein.

In a further embodiment, the reporter molecule may comprise a fluorescein conjugated with a macromolecule and the marker molecule may comprise a rhodamine dye conjugated with a macromolecule.

Figure 2:
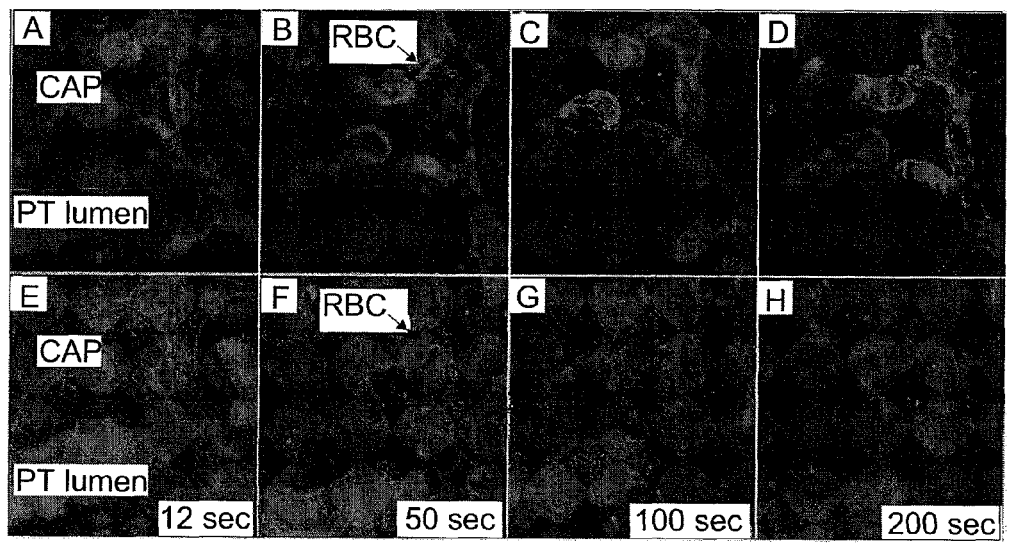
FIG. 2 is a series of micrographs showing renal clearance of a small molecular weight dextran in a normal rat as visualized by intravital 2-photon microscopy. Micrographs taken from a time series reveal localization of both a small FITC-inulin (5.5 kD) (lower series of micrographs) and a large 500 kD Texas Red® dextran (upper series of micrographs) within the capillaries (CAP). The inulin is rapidly filtered into the proximal tubular lumen (PT lumen) resulting in a steady decrease in fluorescence signal over time (panels E, F, G, & H). In contrast, the 500 kD dextran is not cleared and its signal remains constant within the capillaries (panels A, B, C, & D). The fluorescence seen in the PT lumen in Panel A, B, & C is not clearance of the 500 kD dextran but bleed through emissions from the FITC-inulin. The current approach of sequential excitation and acquisition with separate LED's will minimize this bleed through phenomenon.

FIG. 2 contains several fluorescence intensity images of the kidney from a live and healthy male rat. These images were taken as function of time after a bolus intravenous infusion of a dye mixture containing a FITC-inulin (5.5 kD) and 500 kD dextran labeled with a sulforhodamine 101, i.e. Texas Red®. The fluorescence intensity signal from FITC-inulin is shown in the lower series of micrographs, and the 500 kD Texas Red® dextran intensity is shown in the upper series of micrographs. At about 12 seconds after dye infusion, the fluorescence intensity was seen in both the capillaries of the kidney and in the proximal tubule (PT) lumen. The variations in the blood vessel over time indicate that both the FITC-inulin and 500 kD Texas Red® dextran were in these blood vessels. At 50 seconds, the FITC-inulin was already decreasing in intensity in the capillary and in the PT lumen as a result of immediate plasma clearance (glomerular filtration) of this molecule. This was not true for the red 500 kD dextran where the capillary intensity was similar to the 12 second value. A red blood cell (RBC) appears as a dark object as it excludes dye. At 100 and 200 seconds the FITC-inulin intensity continued to decrease in the capillary and in the PT lumen as filtration continued to remove it from the body. This again was not true for the 500 kD Texas Red® dextran which did not change in intensity during this time interval as it was not filtered. Consequently, the relative strength of the intensity from the blood vessels increases indicating a relative increase in the 500 kD Texas Red® dextran to FITC-inulin concentration ratio due to plasma clearance of the FITC-inulin. This type of time-series image collection contains dynamic information about a given molecule passing through the glomerular filtration barrier of the kidney, and becoming part of the filtrate. This provides the basis for the inventors' measurement of plasma clearance rates and GFR.

Figure 3:
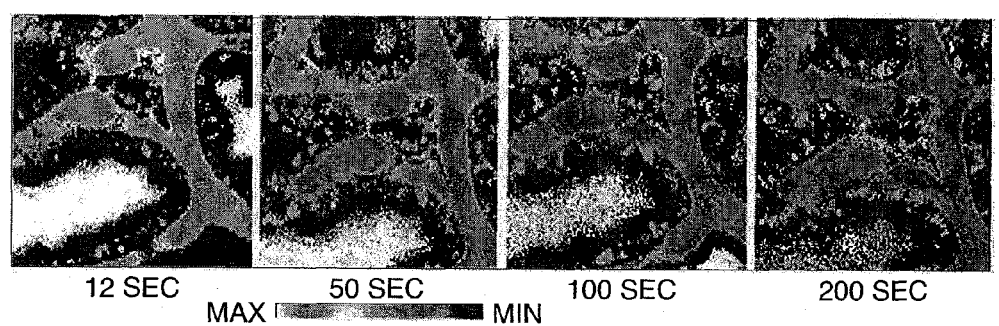
FIG. 3 is a series of micrographs showing the intensity ratio of FITC-inulin to the 500 kD Texas Red® dextran with the 500 kD Texas Red® dextran staying in the blood stream a longer time after dye infusion due to the larger molecular size.

To quantify molecular filtration dynamics, the inventors used the intensity ratio of the FITC-inulin and the 500 kD Texas Red® dextran (See FIG. 3). The intensity ratio from the blood vessels in FIG. 3 changes over time with a change of relative concentrations of the two dyes. Since the 500 kD dextran molecules are minimally cleared from the vascular culture, not by the kidneys, due to its large size, it remains stable in the plasma for a long time after infusion. Typically, there was no noticeable intensity drop from the 500 kD dextran within the time period following a dye infusion (anywhere between 5-30 minutes). This resulted in a decreasing intensity ratio visualized over time. It is this type of ratio that greatly minimizes the problems with using fluorescence intensity as a read out for biological studies.

Figure 4:
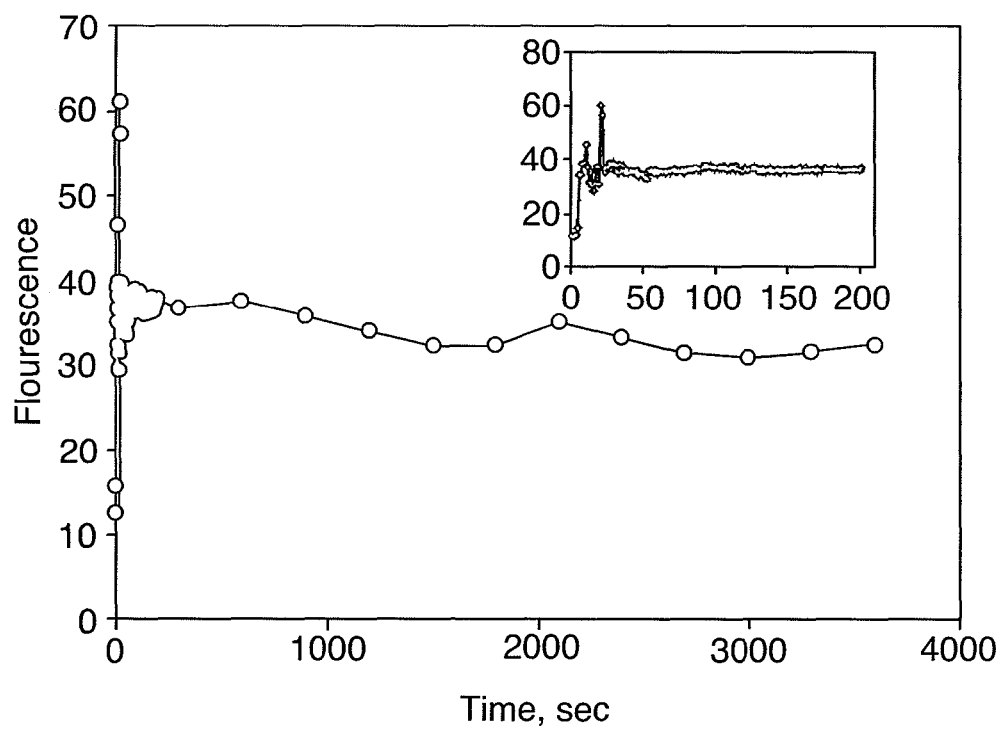
FIG. 4 is a plot of the intensity time-series of the 500 kD FITC dextran measured from a blood vessel following a bolus infusion up to 60 minutes.

The inventors have also used a 500 kD fluorescent dextran for similar studies in order to further minimize filtration and extend the dye's plasma survival time. FIG. 4 is an example of the intensity time-series of the 500 kD FITC dextran measured from a blood vessel following a bolus infusion up to 60 minutes. The initial intensity spike (see inlet) was due to dye injection and fast distribution of the dye molecules into the whole plasma volume. It did not show significant intensity drop for the rest of the curve. Effectively, the decrease of the fluorescence intensity ratio of labeled inulin to labeled 500 kD dextran correlates with the concentration decrease of the labeled inulin.

Figure 5:
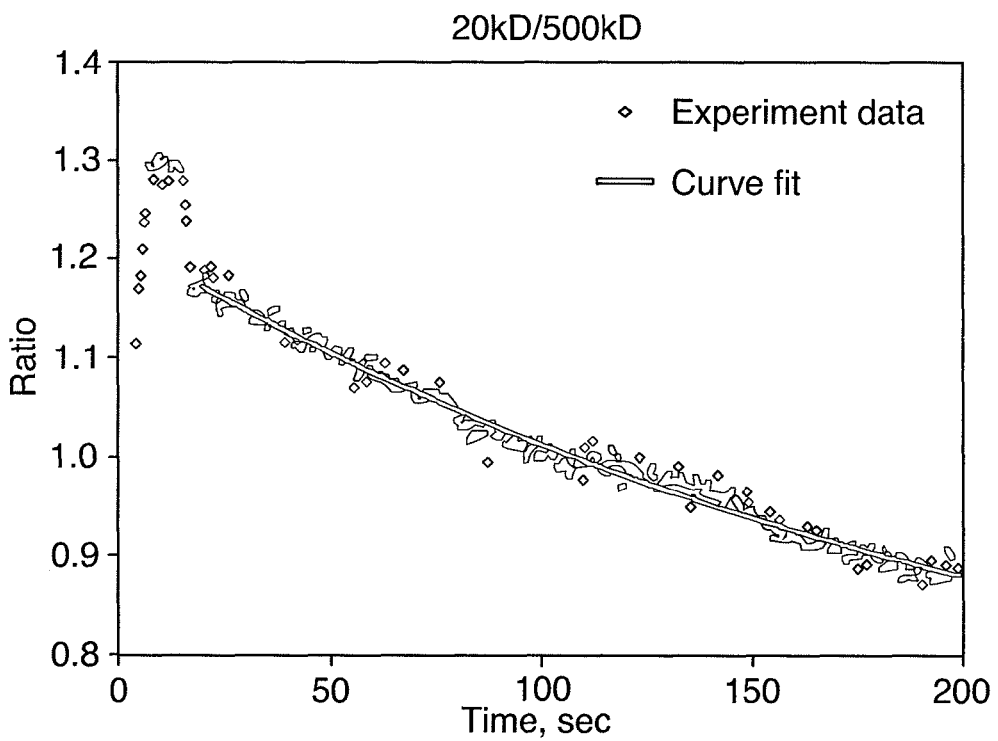
FIG. 5 is a plot of the intensity ratio of a bolus injection of 20 kD FITC dextran to 500 kD Texas Red® dextran as a function of time along with the result of a least square fit.

FIG. 5 is a plot of the intensity ratio of a bolus injection of 20 kD FITC dextran to 500 kD Texas Red® dextran as a function of time along with the result of a least square fit. Each data point in FIG. 5 was the average ratio value of the same region from a blood vessel extracted from an image time-series (such as the images shown in FIG. 3). The data points were plotted every 0.5 seconds up to 200 seconds. The decay occurred in two phases, the initial phase and the clearance phase (or the filtration phase/elimination phase). The gradual increase of the initial phase was due to relative dye distributions and accumulations in the kidney following IV injection. The highest point (around 12 seconds) of the curve marks the starting point of the clearance phase and correlates with the beginning of the appearance of FITC-inulin in the proximal tubule.

The data points of the clearance phase fit well with a single exponential. The inventors obtained a 20 kD FITC dextran plasma clearance rate constant, k, of 0.00458 ($s^{-1}$) (using 95% confidence limits).

Following a bolus infusion of GFR reporter molecules, the plasma concentration of the GFR reporter molecules decreases as a function of time due to renal clearance. By acquiring plasma samples at different time points, one can either directly calculate or perform least square fit of the time trace to retrieve the rate constant (k). GFR can then be determined according to the equation:

$$GFR = kV_d \quad (1)$$

where k is the rate constant and $V_d$ is the total extracellular volume of distribution into which the GFR reporter is diluted. GFR measured using this technique has been validated in patients with stable renal function as well as in rodents and proven to be accurate and correlated well with what was measured using other methods.

Figure 6:
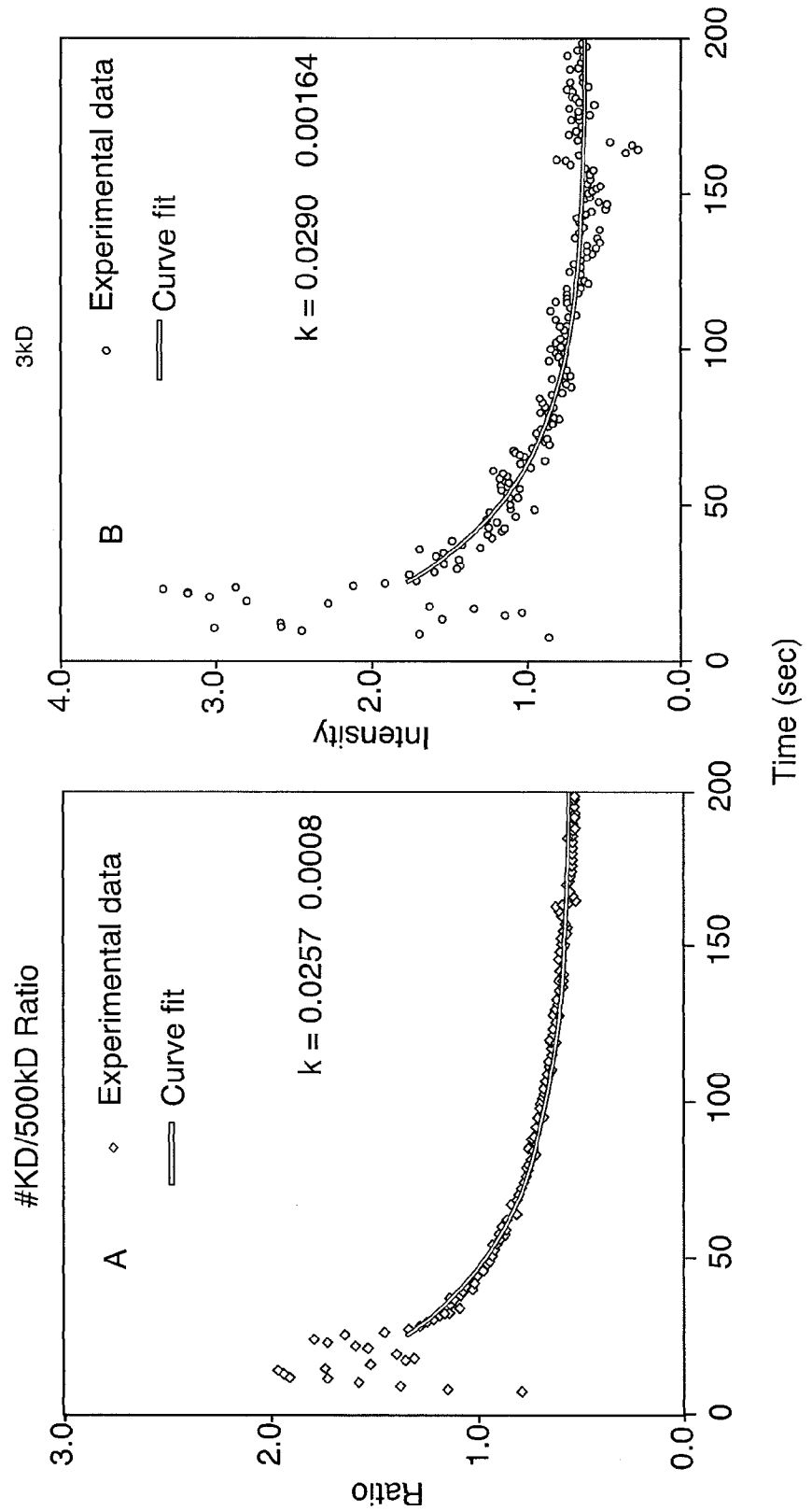
FIG. 6 is a comparison of plots between using a ratio technique and directly using intensity for measuring plasma clearance.

A comparison between using the intensity ratio and directly using the intensity value of a 3 kD FITC conjugated dextran (3 kD FITC dextran) for measuring the clearance rate is shown in FIG. 6. The chief differences are significantly less noise and better identification of distribution phase.

The intensity fluctuations of the 3 kD FITC dextran alone were quite significant (FIG. 6-B). Consequently, the fitting result of the clearance rate constant k contained larger errors and was less defined. In contrast, the intensity ratio (between 3 kD FITC dextran and a 500 kD Texas Red® dextran) had significantly less noise, and the measured clearance rate constant k was much better defined with only 3% error. This was partially because fluorescence intensity is typically very sensitive to even a slight change in microscope focus and movement of the sample. The intensity ratio, on the other hand, is insensitive to minor changes in imaging depth and motion. The inventors are focusing on the fluorescence signals from the blood. Furthermore, the intensity signal of a dye from the blood can change when the blood flow rate changes. However, the relative intensity ratio between two molecules does not change even when the blood flow rate or blood volume changes (assuming there is no clearance). This is because both dye molecules are present in the blood and move together. The method developed by the inventors limits this problem.

The separation between the initial dye distribution and the clearance phase is well-defined using the intensity ratio. When using the intensity of a single dye alone, it is more difficult to determine at what time point the clearance phase begins. The highest data point in the intensity curve typically does not correlate in time with the appearance of the smaller molecule in the proximal tubule lumen. Therefore, the dye distribution and the filtration phases are convoluted in the intensity only curve. Using multi-photon microscopy approaches allow such correlations and is highly beneficial.

It is believed that purity, in terms of size or molecular weight distribution, of the reporter molecule or the marker molecule is vitally important. In addition, the distribution of molecular weight plays an important role in how well GFR can be measured. It is critical that the reporter molecule or the marker molecule should have a distribution such that the reporter molecule or the marker molecule has a glomerular sieving coefficient (GSC) within the range of the present invention, i.e., GSC for the reporter molecule from about 0.5 to about 1.0, and GSC for the marker molecule about 0.0 to about 0.5. For example, even though dextrans are widely used in medical applications, these previous applications did not require the more stringent size control needed for use in the present invention.

Figure 7:
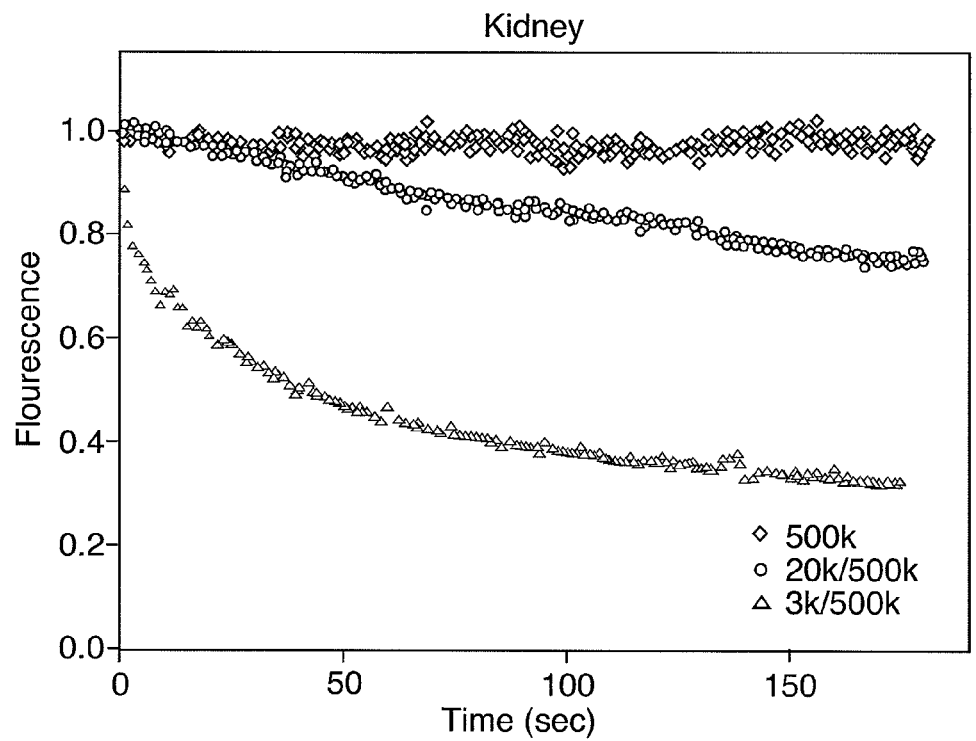
FIG. 7 is a plot showing the kidney vascular plasma intensity ratios resulting over time from two rats after bolus infusion, one with a mixture of 3 kD FITC dextran and 500 kD Texas-Red dextran and the other with 20 kD FITC dextran and 500 kD Texas Red® dextran.

Referring to FIG. 7, a plot of intensity values obtained from two rats after bolus infusion is illustrated. One rat was infused with a mixture of 3 kD FITC dextran and 500 kD Texas Red® dextran. The second rat was infused with 20 kD FITC dextran and 500 kD Texas Red® dextran. The plot shows a rapid decay with the 3 kD/500 kD fluorescence ratio curve. This indicates a fast clearance with movement into the interstitial space. However, a substantial part of it is due to non-renal plasma clearance as seen from 10 kD dextran data of liver imaging illustrated in FIG. 8.

Figure 8:
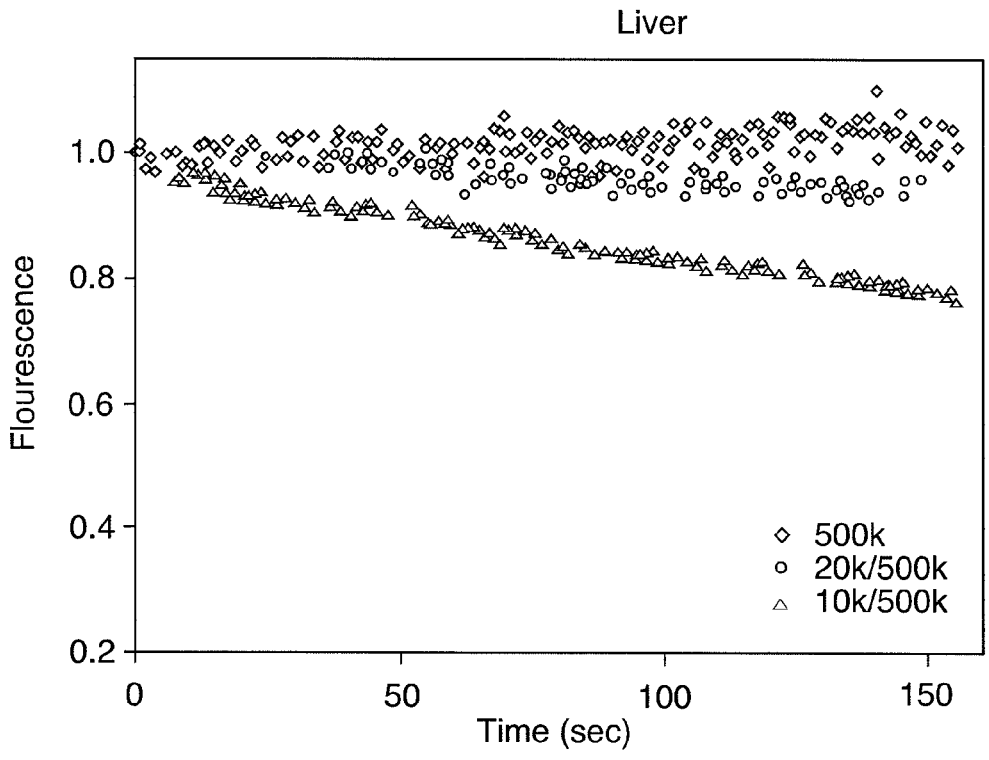
FIG. 8 is a plot showing liver vascular plasma intensity ratios over time from two anephric rats, one injected with a mixture of 10 kD FITC dextran and 500 kD Texas Red® dextran, the other with a mixture of 20 kD FITC dextran and 500 kD Texas Red® dextran.

FIG. 8 was generated from a pair of anephric rats (with both kidneys removed). One of the rats was injected with a mixture of 10 kD FITC dextran and 500 kD Texas Red® dextran. The other rat was injected with a mixture of 20 kD FITC dextran and 500 kD Texas Red® dextran. The 10 kD/500 kD ratio curve shows that there is clear evidence that non-renal plasma clearance of 10 kD dextran is still substantial. Meanwhile, the 20 kD dextran, which can be filtered by glomeruli, shows minimal non-renal plasma clearance. Therefore, it can be used to determine GFR.

Fluorescent Detector

The fluorescent detector 200 includes software for reading and reporting data, a user interface 202 to control the apparatus 10 and review results, and an apparatus for sending and receiving fluorescent signals 204 (see FIGS. 9, 10, and 12-14). This unit 200 is designed to be compatible with a standard IV pump stand, or it can be operated on a table top. It incorporates a battery backup system that is capable of running for 2 hours without connection to AC power.

The user interface 202 is capable of being used by any clinician. It includes touch screen technology for most of the software user interface. This provides flexibility in how the data is shown to the clinicians.

Based on the body of work done to perfect the ratio technique using multi-photon microscopy, the inventors determined that a light transfer probe placed in the blood stream of a subject would be capable of measuring the fluorescent molecules. The current method of using multi-photon microscopy is responsible for generating much of the variation due to the drop off in fluorescence intensity as the tissue is penetrated more deeply. Using a light transfer probe as disclosed herein will eliminate these variations since the measurements will be taken in real time, or substantially real time, directly in the blood. The light transfer probe is explained in more detail below.

Figure 9:
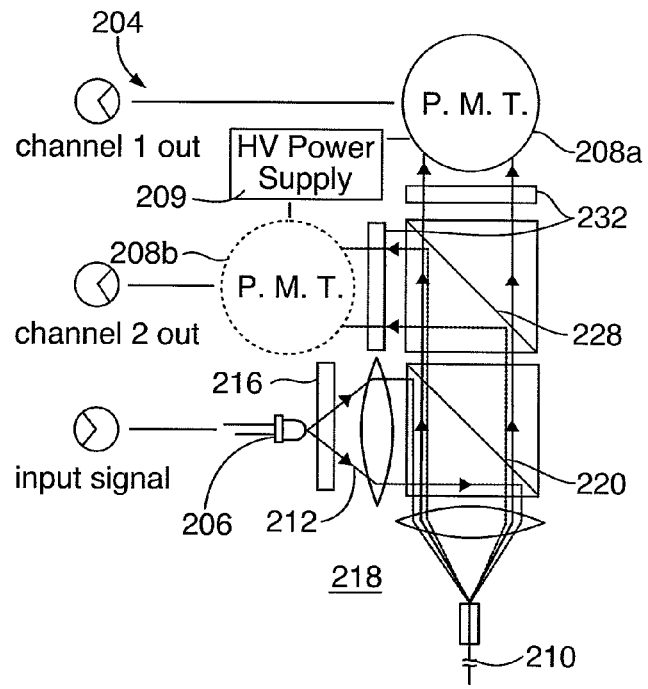
FIG. 9 is a block diagram a system of the present invention.
Figure 10:
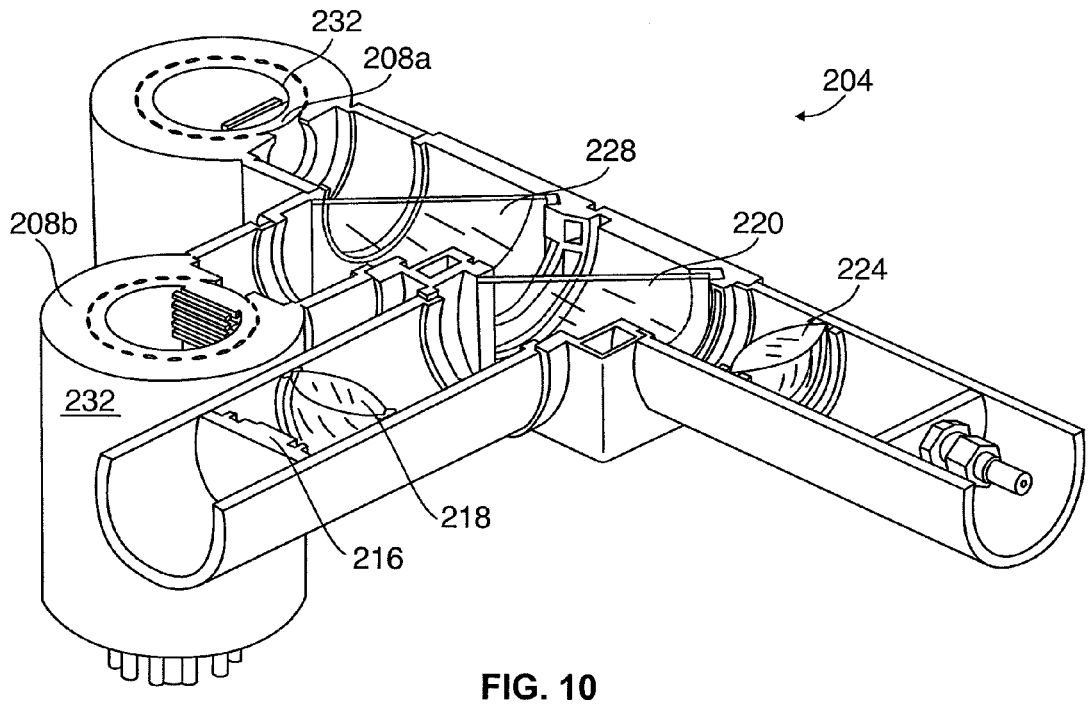
FIG. 10 is a model of the system of FIG. 9.

FIGS. 9 and 10 illustrate a two channel apparatus 204 using a single multi-colored LED 206 (light emitting diode) as a light source. An objective of this apparatus 204 is to determine how much fluorescent signal would be returned from a fiber optic element 210. FIGS. 9 and 10 show both a diagram and computer model of the optical system used in this device. The apparatus includes photo multiplier tubes (PMT) 208a,b as detectors, since these devices have well-known characteristics. Alternatively, the detector may be a photo detector, a solid state detector, a charge-coupled device, or any other equivalent device without departing from the spirit of the invention. This apparatus may have one or more power supplies 207,209, and/or controllers, for providing power to the LED 206 and PMTs 208a,b.

An optical path 212 focuses the light from an LED source 206 through a selection of band pass 216 and dichroic filters 220, then onto the fiber optic element 210. An excitation light is then passed down the fiber optic element 210 into a test solution chosen to simulate the approximate level of fluorescent dextrans in a blood stream. The fiber optic element 210 is generally a fiber optic cable in the range of 0.5 to 1 mm in diameter or even smaller.

Once excited, a small portion of the fluorescence signal then passes back through the fiber optic element 210. The signal then passes through a focusing lens 224, dichroic beam splitter 228 and band pass filter 232 before landing on the cathode of the PMT 208a.

Figure 11:
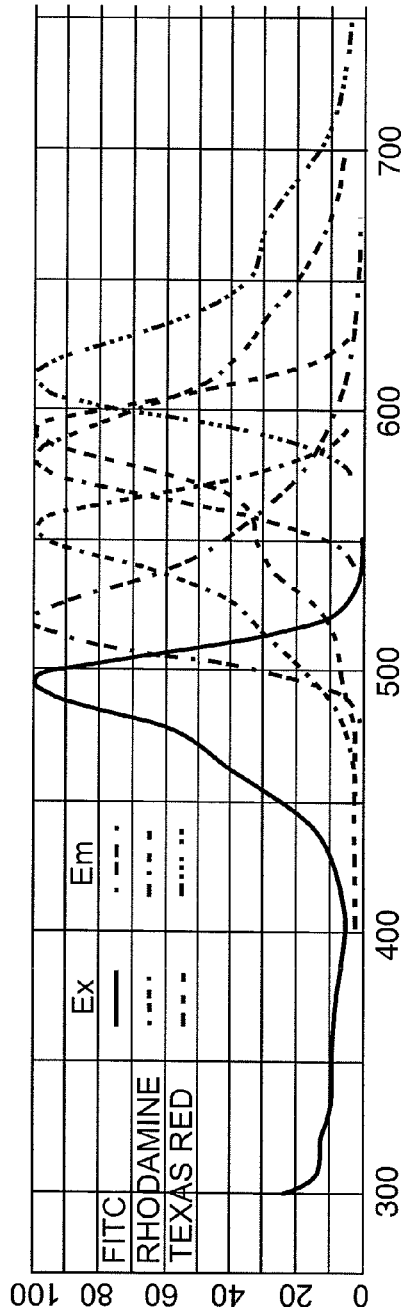
FIG. 11 is a plot of excitation and emission spectra of FITC, rhodamine and Texas Red® dyes.

An easily detectable fluorescent signal is measured from the PMT 208a,b for fluorescein dye. This dye has an excitation peak of about 494 nm and emits light in a broad band of wavelengths centered on 519 nm. Fluorescein dye is only one example of a marker dye. A rhodamine dye may also be used; however, the LED source 206 must have sufficient intensity to excite the rhodamine dye. The spectral response of fluorescein, rhodamine and Texas Red®, can be seen in FIG. 11.

The emergence of white LEDs based on adding a phosphor to the LED die may be used in the present device 200, but the narrow spectral bandwidth associated with standard LEDs is superior for reducing background light. The intensity of the light source and how efficiently energy can be delivered to the fiber optic 210 is critical.

Laser diodes may be used as a substitute for LEDs. The laser diode provides additional light energy which may allow a reduction in the concentration of dye markers in the blood stream. However, most of the wavelengths available are not ideal for the preferred fluorescent molecules of fluorescein and sulforhodamine 101.

LEDs from several vendors have been evaluated. Several LEDs meet the needs of the apparatus. These LEDs provide the best flux density per unit area and work well with the filters providing excellent elimination of off wavelength background.

For fluorescein, a LED490-03U made by ROITHNER LASERTECHNIK GmbH of Austria may be chosen. This LED has a peak wavelength of 490 nm for fluorescein excitation. This LED is rated at 1.2 mw. Alternatively, for fluorescein, an XREBLU-L1-0000-00K01 LED made by Cree Inc. of Durham, N.C. is preferable. This part is a high power surface mount LED with good thermal characteristics. The peak wavelength for this application is 485 nm with a minimum flux output of 30.6 lumens. A surface mount part that can be sorted to have similar characteristics may be substituted for this part.

For sulforhodamine 101 excitation, an 822-OVTL01LGAAS from OPTEK, having distribution in North America and throughout the world, with a peak wavelength of 595 nm, may be used. This surface mount LED has a higher flux density, so it can be run at lower power settings to minimize wavelength thermal drift. The target output power for the 1 mm fiber optic will be about 50 microwatts. For sulphorhodamine 101 excitation, an XRCAMB-L1-0000-00K01 LED from Cree Inc. of Durham, N.C. is preferable. LEDs of this type can be sorted for peak wavelength over the range of 585 nm to 595 nm. A peak output of 590 nm has been chosen for the application. These are high power surface mount LEDs with good thermal characteristics. The luminous flux output of this LED is also 30.6 lumens.

Filter selection is critical to performance of this system. Since the fluorescence signal returning through the fiber optic 210 will be many orders of magnitude below the excitation energy, filter blocking and bandpass characteristics are critical to proper performance. The fluorescent markers which have been used in microscopy and other applications for many years are well known in the art. Thus, excellent filter sets are available from a variety of manufacturers such as SEMROCK of the United States. These filters are ideal for this application.

Figure 12:
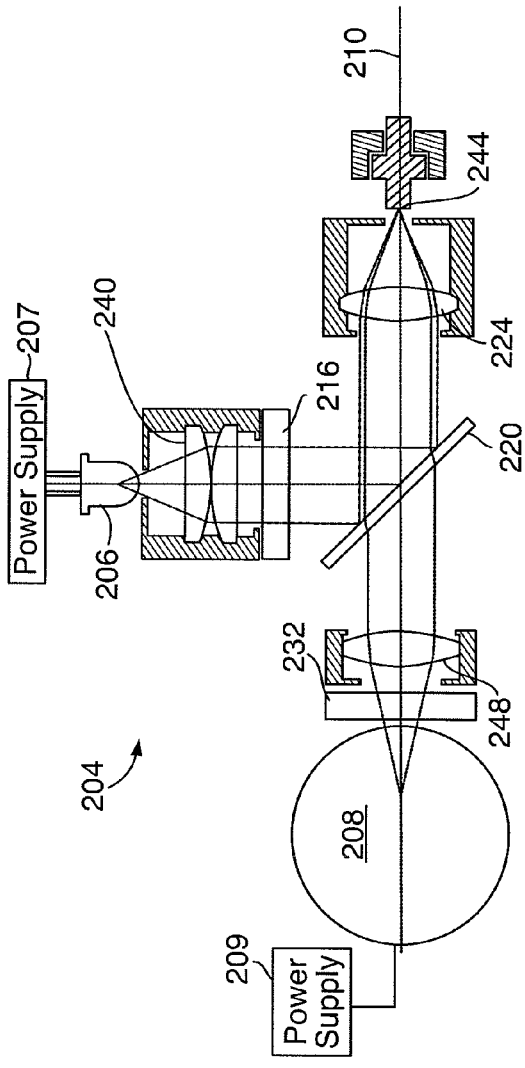
FIG. 12 is a block diagram of a single channel optical system.
Figure 13:
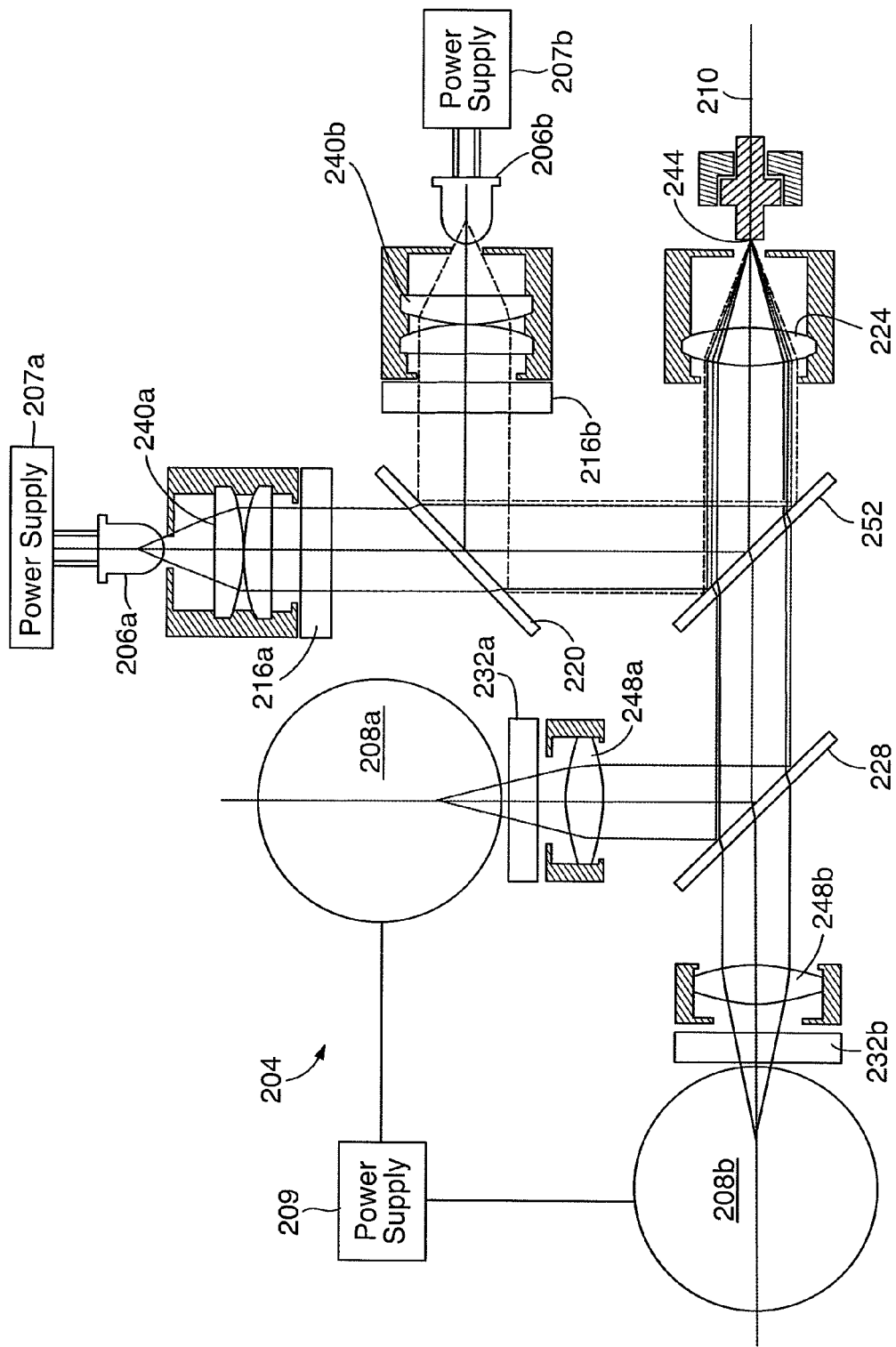
FIG. 13 is a block diagram of a two channel optical system.

Two additional apparatuses for sending and receiving fluorescent signals 204 have been contemplated by the inventors. These apparatuses are illustrated in FIGS. 12 and 13 and are aimed at improved optical geometry. A single channel apparatus is illustrated in FIG. 12. One objective of the single channel device is to improve the signal to background ratio and determine the target signal strengths for the fluorescently tagged dextrans in whole blood. An improved optical geometry has significantly reduced the background levels over an order of magnitude. This new optical geometry and fiber coupling has provided us with a 30 to 1 signal to background ratio.

FIG. 12 is a block diagram of a single channel optical system. The single channel device shown in FIG. 12 uses a simple optical design. Light from a 490 nm LED 206 is relayed through a band pass dichroic filter 220, then focused onto the fiber optic surface mount adaptor (SMA) connector 244. A simple condenser lens element 240 is used to minimize spherical aberrations that would limit ability to focus onto the small 0.5 to 1 mm fiber optic target 210. The fiber lens 224 works as both a final focusing element for the source light and the initial collimator for the fluorescent emission. The fluorescent emission light is relayed back through the dichroic filter 220 and refocused onto the PMT 208. Simple bi-convex lenses 248 are used for this since the target size on the PMT 208 is not critical, and a FITC emission filter is provided as a band pass filter. Close attention is given to stray light and reflections in this system by utilizing good light absorbing coating materials in the component construction.

Figure 14:
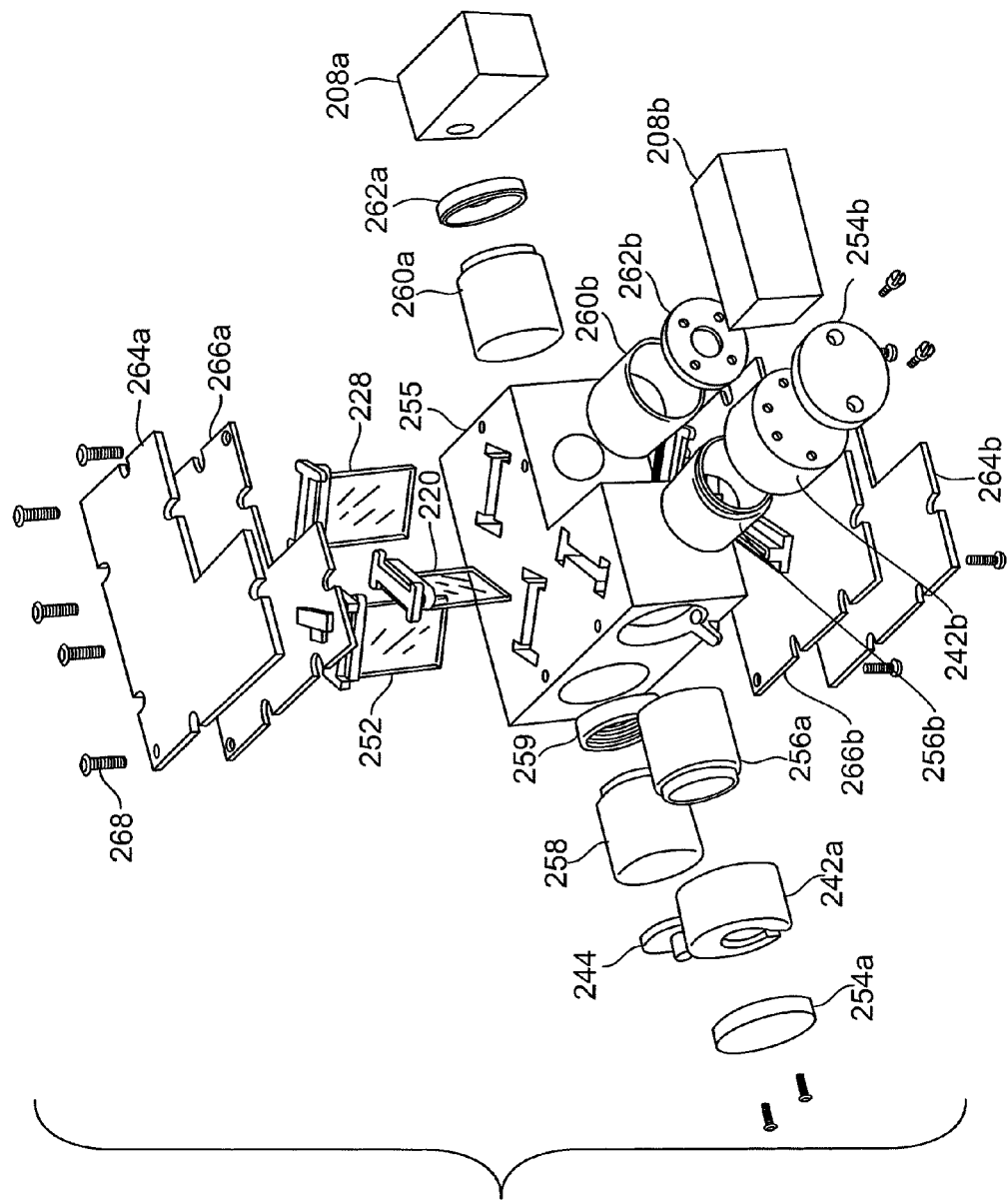
FIG. 14 is an exploded view of the two channel optical system of FIG. 13.

Referring to FIGS. 13 and 14, a two channel optical system is illustrated. Similar components to those chosen in the single channel design are used in the two channel design. The main differences are an additional dichroic filter within holders 254a,b and spaced from a main block 255 by spacers 256a,b used to combine light from the 490 nm LED 206a and 595 nm LED 206b together. Each source utilizes its own condenser lens assembly 240a,b and band-pass filter 216a,b, a 595 nm filter and a 490 nm filter respectively, within holders 242a,b. The light beams from the LEDs 206a,b are then relayed through a special dual band dichroic filter 252 before being focused by the lens 224 onto the fiber coupler 244, specifically the fiber optic target 210. This dual band filter is readily available from SEMROCK. The emission from both fluorescent molecules then travels back through the fiber optic cable 210. The fiber lens 224 is attached to main block 255 within holder 258 and ring 262 and is used to collimate this light for relay back through the dual band dichroic filter 252 and then split to the appropriate PMT 208a,b using a final emission dichroic filter 228. Each PMT assembly 208a,b has a final focusing lens 248a,b and an emission filter 232a,b, preferably a FITC emission filter and a sulphorhodamine 101 emission filter respectively, within holders 260a,b and PMT adaptors 262a,b. Main block 255 is closed by sealing plates 264a,b and gaskets 266a,b with fasteners 268

An electrical circuitry contains a microcontroller to control both the pulse rate to the LEDs 206a,b and synchronize the readings from the PMTs 208a,b. The LEDs 206a,b are energized for a short time at a frequency of 100 Hz. At no time are both LEDs 206a,b illuminated, eliminating some of the bleed through of the two fluorescent markers. A high speed 16 bit analogue/digital converter is used to read the PMTs 208a,b and average the data. A laptop computer may be used for the software component of this system, or the electrical circuitry, microcontroller, and software may be housed within the fluorescent detector 200.

Mathematical Model

A two compartment mathematical model may be used to calculate GFR from the intensity ratio of the two tagged dextran molecules. This model may be included in software which may be stored on an external computer or within the fluorescent detector 200. Alternatively, the mathematical model may be hard wired circuitry either internal or external to the apparatus.

GFR and apparent volume of distribution can be measured by monitoring the plasma disappearance of the fluorescently labeled dextran molecule intravenously administered by a single dose bolus injection. FIG. 15 illustrates a widely used two-compartment model, also known as three-component model. The two compartments in question are vascular space and interstitial space. The basic assumption for this model is that the infused reporter molecule will distribute from the vascular space to interstitial space after the bolus injection, but the marker molecule will be retained in the vascular space. The plasma removal of the reporter molecule only occurs from the vascular space.

The plasma clearance rate and the inter-compartment clearance rate are denoted as G and k, respectively. The plasma volume for the vascular space and interstitial space are $V_1$ and $V_2$, respectively. As demonstrated by Sapirstein et al. (Sapirstein, L. A., D. G. Vidt, et al. (1955). "Volumes of distribution and clearances of intravenously injected creatinine in the dog." *American Journal of Physiology* 181(2): 330-6.) the amount change per unit time in $V_1$ is given by the following equation:

$$V_1 \frac{dC_1}{dt} = -GC_1 - k(C_1 - C_2) \quad (2)$$

Total injected amount D can be expressed as the following:

$$D = C_1 V_1 + C_2 V_2 + G \int_0^t C_1 \, dt \quad (3)$$

where $C_1$ and $C_2$ denote the concentrations of the reporter molecule in the vascular and interstitial space, respectively.

Combining the two equations above yields the following second order linear differential equation (Sapirstein, Vidt et al. 1955):

$$V_1 \frac{d^2 C_1}{dt^2} + \left(\frac{G+k}{V_1} + \frac{k}{V_2}\right)\frac{dC_1}{dt} + \frac{kGC_1}{V_1 V_2} = 0 \quad (4)$$

The general solution to equation (4) is a bi-exponential function expressed in equation (16) below:

$$C_1(t) = Ae^{-\alpha t} + Be^{-\beta t} \quad (5)$$

where the decay constants $\alpha$ and $\beta$ can be expressed in k, G, $V_1$ and $V_2$ (Sapirstein, L. A., D. G. Vidt, et al. (1955). "Volumes of distribution and clearances of intravenously injected creatinine in the dog." *American Journal of Physiology* 181(2): 330-6.).

Assuming the inter-compartment movement is negligible before the intra-compartment mixing in $V_1$ is completed, then the following two boundary conditions at t=0 become valid: $C_0 = D/V_1$ and $C_2 = 0$.

From equations (2), (3), (5), and the two boundary conditions we can derive the following (Sapirstein, L. A., D. G. Vidt, et al. (1955). "Volumes of distribution and clearances of intravenously injected creatinine in the dog." *American Journal of Physiology* 181(2): 330-6.):

$$GFR = \frac{D}{A/\alpha + B/\beta} \quad (6)$$

$$V_1 = \frac{D}{A+B} \quad (7)$$

$$V_d = \frac{D\left(\frac{A}{\alpha^2} + \frac{B}{\beta^2}\right)}{\left(\frac{A}{\alpha} + \frac{B}{\beta}\right)^2} \quad (8)$$

where the total extracellular volume of distribution $V_d$, is the sum of $V_1$ and $V_2$.

Parameters A, B, $\alpha$, and $\beta$ can be obtained by fitting the experimental data to equation (5).

In practice we may obtain the plasma volume $V_1$ using the marker molecule. $V_1$ may be determined using a plasma sample taken from the mammalian subject 10-15 minutes following a bolus infusion of the marker molecule (or a mixture of both reporter and marker molecule). The concentration of the marker molecule in the plasma sample is determined by using a set of standard samples with known marker concentrations. Briefly, the fluorescence intensity of the standard samples may be measured using the optical device disclosed in the present application or any spectrophotometer. The fluorescence intensity should be linearly proportional to the concentration. That is:

C=kF where C is the concentration, F is the fluorescence intensity, and k is a constant determined by the standard samples. With the same device (either the optical device of the present invention or the spectrophotometer), the fluorescence intensity of the marker in the plasma may be measured. The concentration of the marker in the plasma may be therefore determined using the above equation. Since the amount (dose) of the marker molecule given to the subject is a known value, therefore the plasma volume $V_1$ can be determined as follows:

$V_1$=Dose/plasma marker concentration.

If the linear relationship between the concentration and fluorescence intensity holds for the reporter molecule, equation (5) can then be rewritten as:

$$F_1(t) = A_1 e^{-\alpha t} + B_1 e^{-\beta t} \quad (9)$$

where $F_1$ is the fluorescence intensity of the reporter molecule as a function of time. $A_1$ and $B_1$ are constants.

Thus, equations (6) and (8) can be rewritten as follows:

$$GFR = \frac{V_1(A_1 + B_1)}{A_1/\alpha + B_1/\beta} \quad (10)$$

$$V_d = \frac{V_1(A_1 + B_1)\left(\frac{A_1}{\alpha^2} + \frac{B_1}{\beta^2}\right)}{\left(\frac{A_1}{\alpha} + \frac{B_1}{\beta}\right)^2} \quad (11)$$

where equation (10) represents GFR from intensity of a single, freely filterable reporter molecule type, and equation (11) represents the volume distribution associated with a single, freely filterable reporter molecule type.

In addition, since the fluorescence of the marker is a constant over time, equation (9) can be also expressed in terms of fluorescence ratio of the reporter molecule over the marker molecule. Thus, the bi-exponential equation becomes:

$$R(t) = A_2 e^{-\alpha t} + B_2 e^{-\beta t} \quad (12)$$

where R(t) is the fluorescence intensity ratio of the reporter molecule over the marker molecule as a function of time.

Constants $A_2$, $B_2$, $\alpha$, and $\beta$ can be obtained by fitting the experiment data to the above equation. Thus, the clearance GFR and the total volume of distribution can be expressed as:

$$GFR = \frac{V_1(A_2 + B_2)}{A_2/\alpha + B_2/\beta} \quad (13)$$

$$V_d = \frac{V_1(A_2 + B_2)\left(\frac{A_2}{\alpha^2} + \frac{B_2}{\beta^2}\right)}{\left(\frac{A_2}{\alpha} + \frac{B_2}{\beta}\right)^2} \quad (14)$$

where equation (13) represents GFR from the intensity ratio between a freely filterable reporter molecule type and a larger marker molecule type, and equation (11) represents the volume distribution associated with from a freely filterable reporter molecule type and a larger marker molecule type.

Evidently, when the inter-compartment volume exchange rate approaches zero, this model collapses to a single compartment model. However, it has been shown that as the plasma clearance level increases this mono-exponential approximation will lead to an overestimation of the GFR (Schwartz, G. J., S. Furth, et al. (2006). "Glomerular filtration rate via plasma iohexol disappearance: pilot study for chronic kidney disease in children." *Kidney International* 69(11): 2070-7; Yu, W., R. M. Sandoval, et al. (2007). "Rapid determination of renal filtration function using an optical ratiometric imaging approach." *American Journal of Physiology—Renal Physiology* 292(6): F1873-80.)

Light Transfer Probe

Figure 17:
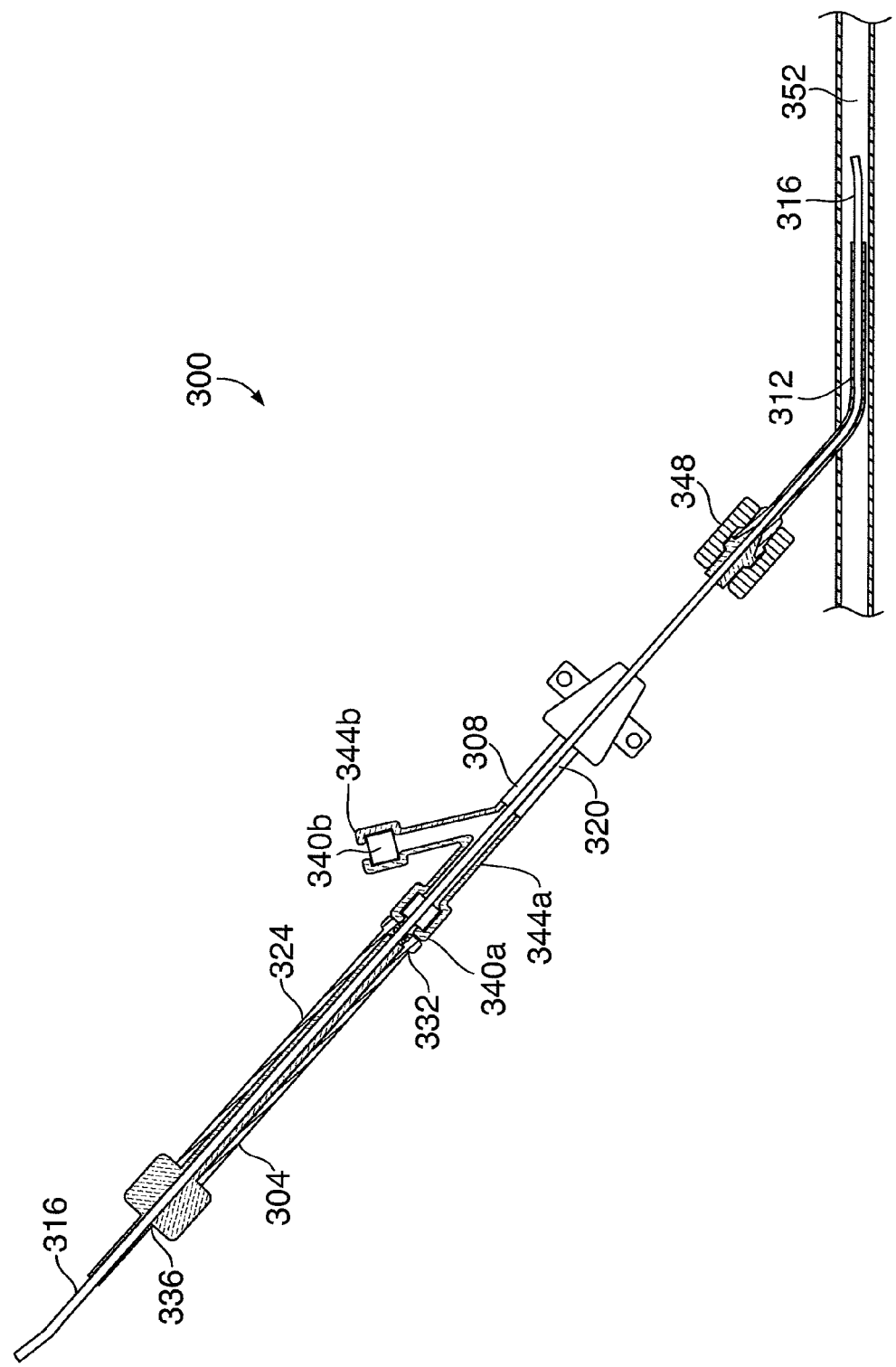
FIG. 17 is an illustration of the light transfer probe of FIG. 16 assembled and inserted within a patient's vein.

Referring to FIGS. 16 and 17, the light transfer probe 300 for use with the present invention is illustrated. The light transfer probe 300 includes a fiber optic insertion tool 304, a dual port lumen 308, and a 18 gauge introducer 312. A standard 1 mm plastic fiber optical cable 316 may be inserted through a passageway 320 defined by a combination of the insertion tool 304 joined with the lumen 308 joined with the introducer 312. Accordingly, each of these components is of a tubular configuration. Preferably, a 0.75 mm fiber optic cable is inserted through the passageway 320. The 0.75 mm diameter was chosen to allow use of a standard 18 gauge introducer.

The insertion tool 304 includes a first tubular member 324 slidable within a second tubular member 328. Fluid-tight seals are provided on opposing ends of the second tubular member 328 by o-rings 332 about the first tubular member 324 and the fiber optic cable 316, respectively. The fiber optic cable 316 is securely held or fixed within the insertion tool 304 by a seal 336 at an opposite end of the insertion tool 304.

The insertion tool 304 is joined to one of the ports 340a on the lumen 308. Hemostatic seals 344a,b are located on the ports 340a,b. The other port 340b is to provide for bolus injection or a continuous infusion of the fluorescent molecule. A luer connector 348 at an opposite end of the luman 308 joins the subject with the introducer 312.

The fiber optic cable 316 may comprise either single or multiple single fibers for light delivery and collection of the emission and excitation. The fiber optic cable 316 is inserted within a subject's vein 352 by pressing the first tubular member 324 and the captive optical cable 316 through the second tubular member 328 wherein the fiber optic cable 316 is extensible from the light transfer probe 300. The optical cable 316 traverses through the subject by the luer connector 348 through the introducer 312 and into the subject's vein 352. The fiber optic cable 316 may have a small permanent bend on an end inserted into the subject's vein 352. This bend helps penetrate the tissue and minimizes interference of the fiber optic cable 316 within the vein.

In use, the fiber optic cable 316 is an extension of, or placed in communication with, the fiber optic cable 210 of the fluorescent detector 200 to transmit a signal or signals generated at the subject's vein to the fluorescent detector 200 for evaluation.

An aspect of the present invention is a method for measuring glomerular filtration rate (GFR) of the kidney a mammalian subject using the above described optical device. The "kidney" as used in the present invention refers to the total kidney function of the mammalian subject. This method comprises: (1) providing a known quantity of a fluorescent reporter molecule and a known quantity of a fluorescent marker molecules wherein the fluorescent reporter molecule is filtered by the kidney of the mammalian subject and the fluorescent marker molecule is retained in the vascular system of the mammalian subject, and wherein the fluorescent reporter molecule and the fluorescent marker molecule are chemically stable in the vascular system during the measurement of the GFR and wherein the fluorescent reporter molecule has a first fluorescence excitation wavelength to generate a first fluorescence emission signal having a first fluorescence emission wavelength and the fluorescent marker molecule has a second fluorescence excitation wavelength to generate a second fluorescence emission signal having a second fluorescence emission wavelength, and wherein the first fluorescence emission wavelength is distinguishable from the second emission wavelength; (2) introducing by bolus injection said fluorescent reporter molecule and said fluorescent marker molecule into a vascular system of the mammalian subject; (3) exciting said fluorescent reporter molecule in the vascular system with a first fluorescence excitation wavelength continuously over a period of time for measuring the GFR to generate a series of first fluorescence emission signals having a first fluorescence emission wavelength and exciting said fluorescent marker molecule in the vascular system with a second fluorescence excitation wavelength continuously over the same period of time for measuring the GFR to generate a series of second fluorescence emission signal having a second fluorescence emission wavelength; (4) measuring an intensity of said first fluorescence emission signal and an intensity of said second fluorescence emission signal subsequent to said introducing step and calculating a ratio of the intensity of said first fluorescence emission signal to the intensity of said second fluorescence emission signal wherein said measuring and calculating steps are performed at predetermined intervals and reported in at least substantially real time; (5) obtaining constants $A_2$, $B_2$, $\alpha$, and $\beta$ by fitting ratio data to the following equation:

$$R(t) = A_2 e^{-\alpha t} + B_2 e^{-\beta t}$$

where R(t) is the fluorescence ratio, as a function of time, of the intensity of said first fluorescence emission signal to the intensity of said second fluorescence emission signal, $A_2$ and $B_2$ are constants; $\alpha$ is a fast phase decay constant; and $\beta$ is a slow phase decay constant; and (6) calculating the GFR using the following equation:

$$GFR = \frac{V_1(A_2 + B_2)}{A_2/\alpha + B_2/\beta}$$

wherein $V_1$ is plasma volume, which can be determined as previously described.

The reporter molecule and the marker molecule may be introduced simultaneously or separately at different time.

EXAMPLE 1

Measurement of GFR in Swine Using Fluorescence Ratiometric Analysis Method

Figure 18:
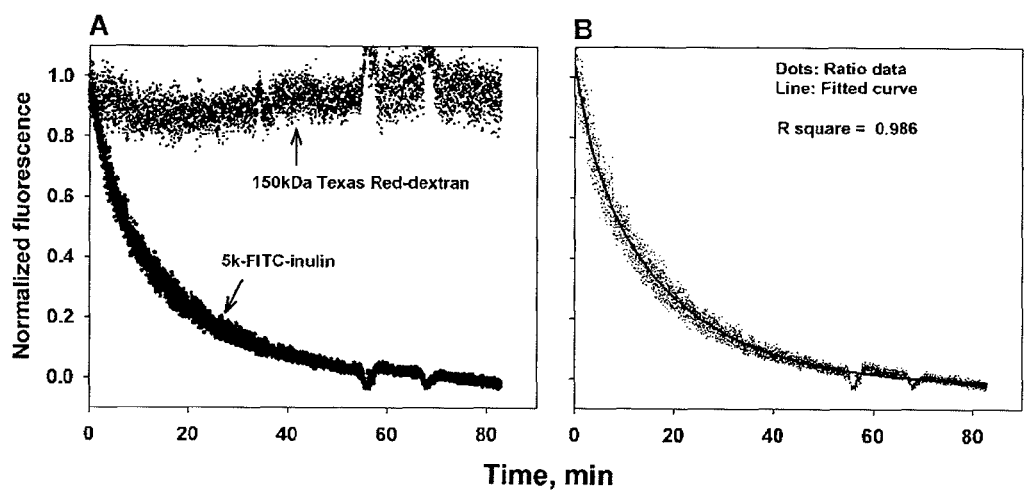
FIG. 18 shows the quantifying of plasma volume and GFR in a pig using fluorescent dextrans. A) Time courses for the reporter 5 kDa-FITC-inulin and the marker 150 kDa Texas Red-dextran after a coinjection to an Osabaw swine. B) The fluorescence ratio (inulin/dextran) data (dots) were fitted to a bi-exponential equation and the fitted curve is shown as a solid line.

The data obtained using the described optical device (also known as the fluorescence ratiometric analysis method herein) from a female Osawbaw swine weighing 29.5 kg are shown in FIG. 18. The anesthetized pig was administered 75 mg 5 kDa FITC-inulin and 75 mg 150 kDa Texas Red-dextran. The fluorescent data after the completion of the mixing in the vascular space following the bolus infusion are shown. FIG. 18A shows the normalized fluorescence time course for both small and large conjugates. While the signal from the large non-filterable dextran (red channel) remained stable over time, the signal of the filterable 5 kDa FITC-inulin (green channel) decreased rapidly initially indicating a combined inter-compartment movement (from the vascular space to the interstitial space) and kidney clearance, which was followed by a slower decay caused only by kidney clearance (from the vascular space). As a result, the time course of the ratio (green/red), shown in FIG. 18B, looks very similar to the time course of 5 kDa FITC-inulin. The plasma volume obtained using the dilution of the large dextran was 1012.3 ml. The GFR determined using the ratio metric two-compartment method described was 2.16 ml/min/kg. The value obtained using iohexol samples drawn for six hours (Schwartz, G. J., A. G. Abraham, S. L. Furth, B. A. Warady, and A. Munoz, *Optimizing iohexol plasma disappearance curves to measure the glomerular filtration rate in children with chronic kidney disease*. Kidney Int, 2009. 77(1): p. 65-71; Schwartz, G. J., S. Furth, S. R. Cole, B. Warady, and A. Munoz, *Glomerular filtration rate via plasma iohexol disappearance: pilot study for chronic kidney disease in children*.

Kidney International, 2006. 69(11): p. 2070-7) from Dr. Schwartz's laboratory at the University of Rochester was 2.02 ml/min/kg.

EXAMPLE 2

Figure 19:
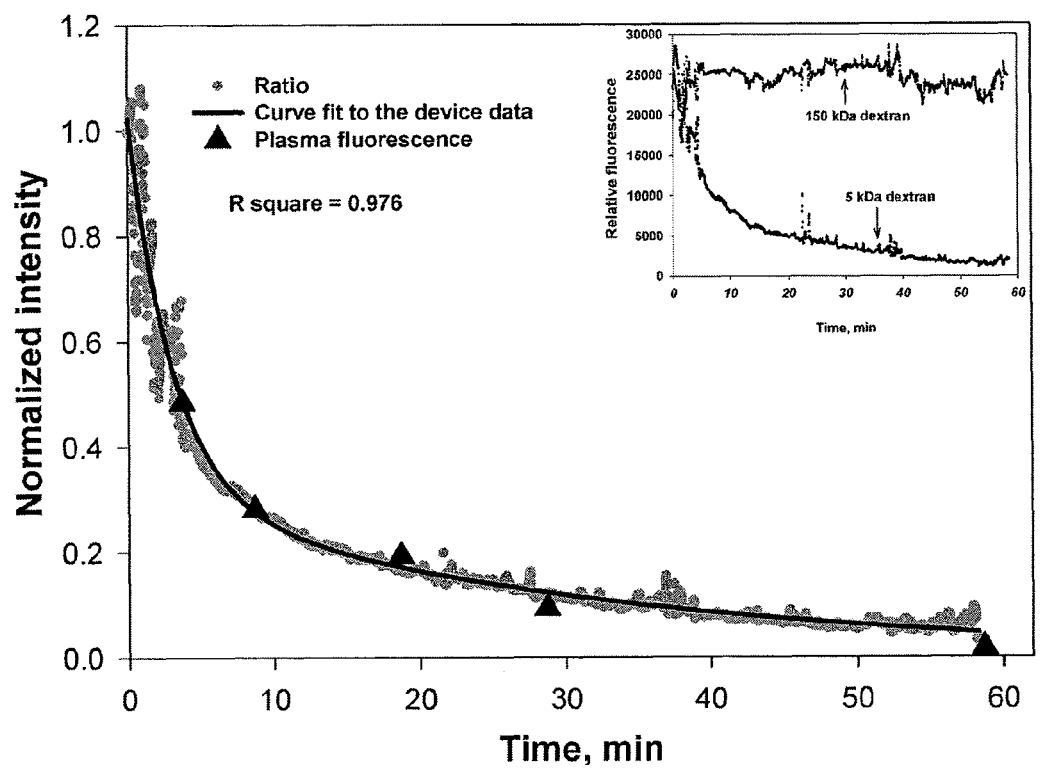
FIG. 19 shows the quantifying of plasma volume and GFR in a dog using fluorescent dextrans. The 5 kDa/150 kDa ratio data (dots) from the optical device were fit to a bi-exponential equation. The fitted curve is shown as a solid line. An excellent overlap is seen between the device data points and the plasma fluorescence of the 5 kDa FITC-dextran (triangles) from a spectroscopic analysis. The original data that generated the ratio are shown as an insert.

Measurement of GFR in Dog Using the Fluorescence Ratiometric Analysis Method Data from the dog study are shown in FIG. 19. The dog was administered 175 mg 5 kDa aminofluorescein-dextran and 75 mg 150 kDa 2-sulfohexamine rhodamine-dextran (2SHR-dextran). The higher noise in the data was caused by the movement during the data collection as the dog was not anesthetized. The plasma volume was determined to be 1720 ml. The GFR of the 33.0 kg dog was determined using three different methods. The value determined from the optical device was 4.49 ml/min/kg and the value obtained from iohexol analysis reported from Dr. Schwartz's laboratory was 4.50 ml/min/kg.

EXAMPLE 3

Corrleation of GFR Determined by Fluorescence Ratiometric Analysis Method and by the Iohexol Plasma Clearance Method in Gentamycin-Induced Acute Kidney Injury (AKI) Dogs Five spayed female young adult hound-type mogrel dogs were confirmed to be in good health based on physical examination, complete blood count, blood chemistry analysis, urinalysis, urine protein-to-creatine ratio (UPC) and aerobic urine culture. Acute tubular necrosis was induced in the 5 dogs with IV gentamycin (10 mg/Kg IV q8 hours for 10 days; first day of injection was Day 0. Serum creatinine, blood urea nitrogen (BUN), urine specific gravity (USG), UPC and GFR via iohexal plasma clearance method and ratiometric fluorescence analysis method were determined on days 3, 6 and 9. All dogs were euthanized on day 9. Table 1 shows the serum creatinine and BUN concentrations, USG and UPC in the five dogs with gentamycin-induced AKI. Greater than 25% increases over baseline serum creatinine, reduced urine concentration ability, and proteinuria occurred in all five study dogs, although kidney injury was insufficient to result in overt azotemia (canine reference ranges: creatinine, 0.5-1.5 mg/dl; BUN, 7-32 mg/dl; UPC, <0.5).

TABLE 1

Vaules of creatinine, BUN, USG and UPC of the gentamycin-induced AKI dogs

| Dog | Day | Creatinine (mg/dl) | BUN (mg/dl) | USG | UPC |
|---|---|---|---|---|---|
| 1 | 0 | 0.9 | 20 | 1.052 | 0.1 |
|   | 3 | 0.9 | 14 | 1.010 | 0.3 |
|   | 6 | 1.0 | 14 | 1.010 | 0.6 |
|   | 9 | 1.5 | 16 | 1.006 | 2.1 |
| 2 | 0 | 0.8 | 20 | 1.014 | 0.1 |
|   | 3 | 0.9 | 16 | 1.008 | 0.5 |
|   | 6 | 1.2 | 22 | 1.009 | 0.5 |
|   | 9 | 5.3 | 97 | 1.011 | 2.8 |
| 3 | 0 | 1.1 | 14 | 1.030 | 0.1 |
|   | 3 | 1.0 | 12 | 1.014 | 1.0 |
|   | 6 | 1.5 | 15 | 1.003 | 0.5 |
|   | 9 | 1.9 | 18 | 1.004 | 3.1 |
| 4 | 0 | 0.9 | 16 | 1.048 | 0.1 |
|   | 3 | 1.0 | 15 | 1.014 | 0.2 |
|   | 6 | 1.4 | 16 | 1.007 | 0.0 |
|   | 9 | 1.6 | 16 | 1.006 | 1.7 |

TABLE 1-continued

Vaules of creatinine, BUN, USG and UPC of the gentamycin-induced AKI dogs

| Dog | Day | Creatinine (mg/dl) | BUN (mg/dl) | USG | UPC |
|---|---|---|---|---|---|
| 5 | 0 | 0.7 | 9 | 1.044 | 0.2 |
|   | 3 | 0.8 | 12 | 1.000 | 0.3 |
|   | 6 | 1.0 | 10 | 1.005 | 0.0 |
|   | 9 | 1.1 | 14 | 1.005 | 1.6 |

To measure the GFR using the iohexol plasma clearance method and the GFR using the fluorescence ratiometric analysis method, the gentamycin-induced AKI dogs were sedated with 0.1 mg/kg of acepromazine maleate IV. 18 gauge, 1.2 inch catheters were placed in one cephalic/antebrachial vein and one lateral saphenous vein. The fiberoptic cable from the optical device described in the present invention was inserted through the cephalic catheter. To correct for possible subclinical plasma volume contraction, 0.9% saline equal to 2.5% of body weight was administered IV over 10 minutes prior to each GFR test. After determination of background fluorescence, 150 mg/kg of iohexol were administered via the saphenous vein. EDTA-anticoagulated blood was collected at 0, 5, 10, 20, 30, 60, 180, 240 and 300 minutes post-injection, centrifuged within 3 hours, and stored at −20° C. Iohexol clearance was determined as previously described by Schwartz et al. (Schwartz, G. J., S. Furth, S. R. Cole, B. Warady, and A. Munoz, *Glomerular filtration rate via plasma iohexol disappearance: pilot study for chronic kidney disease in children*. Kidney International, 2006. 69(11): p. 2070-7). Fiberoptic fluorescence ratiometric GFR determination was performed simultaneously with iohexol clearance. 5 ml of dextran conjugate mixture containing 75 mg 150 kDa 2-sulfohexamine rhoadamine-carboxymethyl dextran and 175 mg 50 kDa 5-amino fluorescein-carboxymethyl dextran was administered through the saphenous vein catheter immediately following iohexol injection. Continuous simultaneous fluorescence was determined for 60 minutes using the optical fiber device of the present invention and GFR was calculated from the concentration-vs.-time fluorescence ratio curve using the 2-compartment model as described in the present invention. Table 2 shows the data for the iohexal clearance and fluorescence ratiometric anlaysis method determined GFR for all the five dogs with AKI over time. Two dogs have repeat results at Day 0 to demonstrate the low coefficient of variation achievable with the ratiometric optical device. Complete data is not available for Dog 5 due to dog- or catheter-associated technical problems during GFR measurement.

TABLE 2

GFR values using the iohexol plasma clearance method and the fluorescence ratiomtric anlayis method in gentamycin-induced AKI dogs

| Dog | Day | GFR: Iohexol Plasma Clearance (mL/min/kg) | GFR: Ratiometric Analyzer (mL/min/kg) |
|---|---|---|---|
| 1 | 0 | 4.40 | 4.60 |
|   | 3 | 3.06 | 2.70 |
|   | 6 | 2.78 | 1.54 |
|   | 9 | 1.87 | 1.50 |
| 2 | 0 | 3.28 | 2.90 |
|   | 0 | 2.77 | 2.40 |
|   | 3 | 2.00 | 1.95 |
|   | 6 | 2.05 | 1.60 |
|   | 9 | 0.10 | 0.68 |

TABLE 2-continued

GFR values using the iohexol plasma clearance method and the
fluorescence ratiomtric anlayis method in gentamycin-induced AKI dogs

| Dog | Day | GFR: Iohexol Plasma Clearance (mL/min/kg) | GFR: Ratiometric Analyzer (mL/min/kg) |
|---|---|---|---|
| 3 | 0 | 4.00 | 3.10 |
|   | 0 | 3.71 | 3.20 |
|   | 3 | 3.45 | 2.40 |
|   | 6 | 2.46 | 2.16 |
|   | 9 | 1.49 | 1.23 |
| 4 | 0 | 3.82 | 3.05 |
|   | 3 | 2.05 | 1.54 |
|   | 6 | 1.44 | 1.30 |
|   | 9 | 2.47 | 1.40 |
| 5 | 0 | 4.49 | 4.20 |
|   | 3 | 4.17 | 4.10 |
|   | 6 | 3.36 | no data |
|   | 9 | no data | no data |

Figure 20:
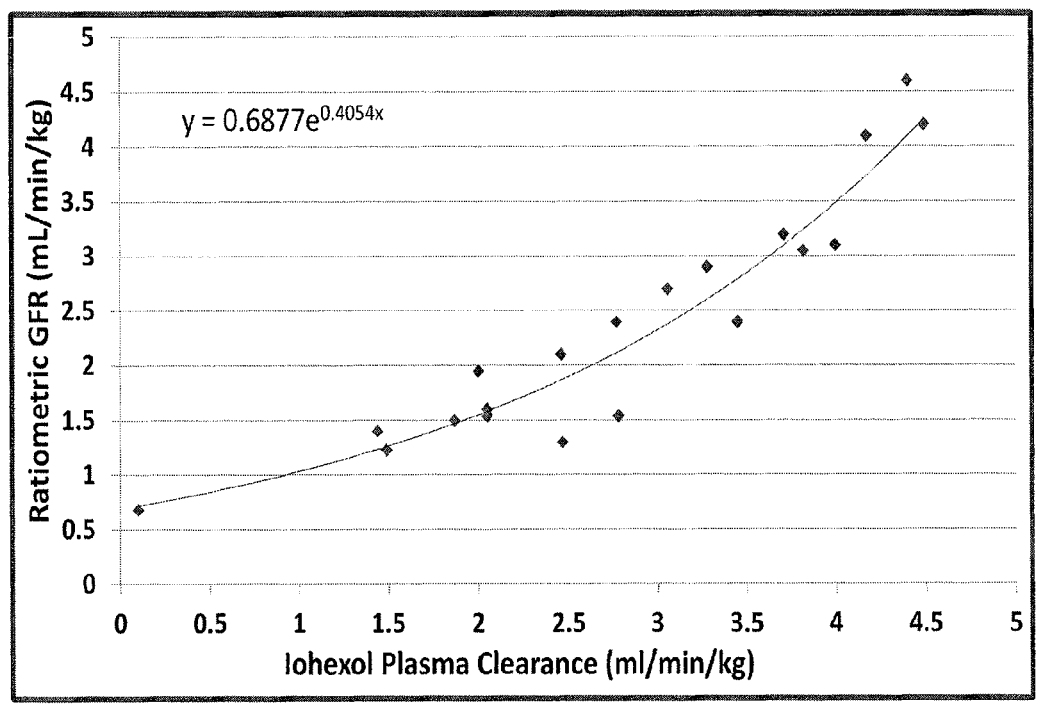
FIG. 20 shows that the GFR determined by fluorescence ratiometric analysis has excellent correlation ($r_s$=0.92; P<0.001) with iohexol plasma clearance.
Figure 21:
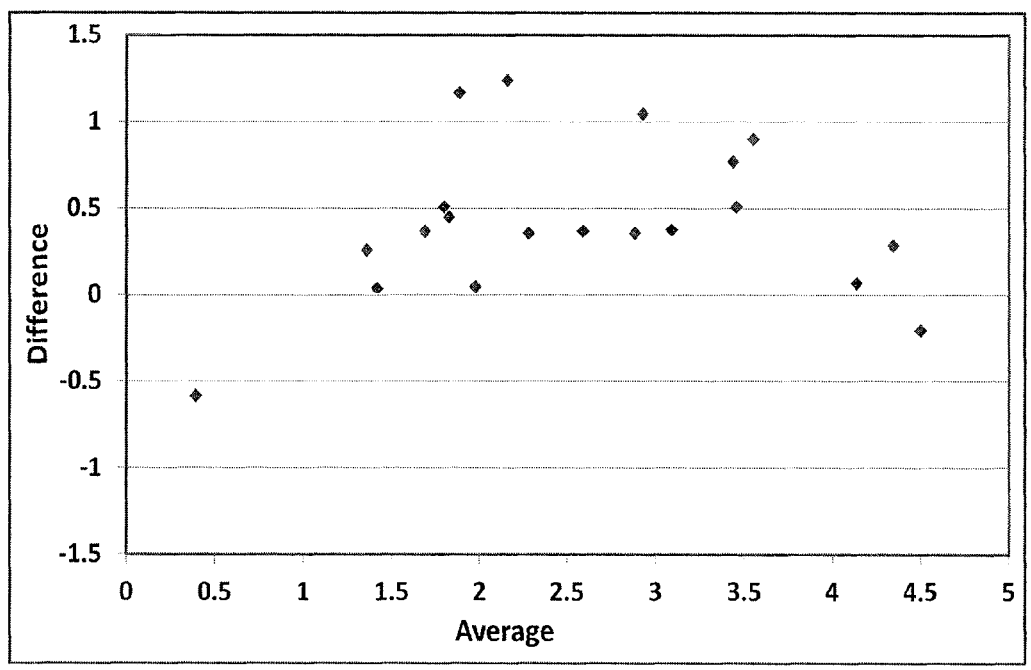
FIG. 21 shows the data for the Bland-Altman difference plots demonstrating that fluorescence ratiometric analysis$_{appears}$ to slightly (0.1-1.25 ml/min/Kg) underestimate GFR across most observed values.

Correlation between fluorescence ratiometric GFR and iohexol plasma clearance was determined using the Spearman's rank correlation coefficient ($r_s$); significance was set at $P<0.05$. Limits of agreement were analyzed using Bland-Altman analysis. FIG. 20 shows that the GFR determined by fluorescence ratiometric analysis has excellent correlation ($r_s=0.92$; $P<0.001$) with iohexol plasma clearance. FIG. 21 shows the data for the Bland-Altman difference plots demonstrating that fluorescence ratiometric analysis appears to slightly (0.1-1.25 ml/min/Kg) underestimate GFR across most observed values. The data in this study shows that the fluorescence ratiometric analysis method of determination of GFR has excellent correlation and agreement with iohexol plasma clearance GFR over a wide range of values. The optical device of the present invention used in these studies allow rapid point-of-care GFR measurements in a large animal model with homologous vessel location and size to the antebrachial vein. Unlike alternative GFR measurement techniques, flourescence ratiometric analyis can be completed within one hour with generation of real-time bedside curves. In addition, there are no apparent toxic effects in any of the study dogs secondary to intravenous infusion of fluorescently labeled detrans.

While the specific embodiments have been illustrated and described, numerous modifications come to mind without significantly departing from the spirit of the invention, and the scope of protection is only limited by the scope of the accompanying Claims.

What is claimed is:

1. A system for measuring the fluorescence intensity of a reporter fluorescent molecule and a marker fluorescent molecule in a vascular system of a mammalian subject to determine glomerular filtration rate (GFR) of the kidney of the mammalian subject, the system comprising:

a source of said reporter fluorescent molecule and said marker fluorescent molecule;

a means for introducing said reporter fluorescent molecule and said marker fluorescent molecule into the vascular system of the mammalian subject;

a means for measuring the fluorescence intensity of said reporter fluorescent molecule and said marker fluorescent molecule within the vascular system of the mammalian subject;

a means for determining an intensity ratio of the fluorescence intensity of said measured reporter fluorescent molecule and marker fluorescent molecule within the vascular system of the mammalian subject, and a means for calculating glomerular filtration rate (GFR) of the mammalian subject according to the equation:

$$GFR = \frac{V_1(A_2 + B_2)}{A_2/\alpha + B_2/\beta}$$

wherein $V_1$ is plasma volume; $A_2$ and $B_2$ are constants; $\alpha$ is a fast phase decay constant; and $\beta$ is a slow phase decay constant;

wherein the ratio of intensity R(t) of the reporter fluorescent molecule and the marker fluorescent molecule are calculated at predetermined intervals; and wherein the constants $A_2$, $B_2$, $\alpha$ and $\beta$ are calculated by fitting the ratio of intensity data to the following equation:

$$R(t) = A_2 e^{\alpha t} + B_2 e^{-\beta t}$$

where R(t) is the ratio of intensity as a function of time;

wherein said reporter molecule is filtered by the kidney of the mammalian subject, and said marker molecule is retained in the vascular system of the mammalian subject; and wherein said reporter molecule and said marker molecule are chemically stable in the vascular system during measurement of kidney function.

2. The system of claim 1 wherein said means for introducing includes a catheter.

3. The system of claim 1 wherein said means for measuring includes an optic fiber in communication with a detector.

4. The system of claim 1 wherein said reporter molecule has a first fluorescent characteristic, and said marker molecule has a second fluorescent characteristic, and wherein said first fluorescent characteristic and second fluorescent characteristic are distinguishable.

5. The system of claim 4 wherein the first fluorescent characteristic is a first excitation wavelength and a first emission wavelength and the second fluorescent characteristic is a second excitation wavelength and a second emission wavelength, said first and second fluorescence excitation wavelengths and said first and second fluorescence emission wavelengths being unequal.

* * * * *

UNITED STATES PATENT AND TRADEMARK OFFICE
CERTIFICATE OF CORRECTION

PATENT NO.         : 8,591,865 B2
APPLICATION NO.    : 12/946471
DATED              : November 26, 2013
INVENTOR(S)        : Exing Wang et al.

It is certified that error appears in the above-identified patent and that said Letters Patent is hereby corrected as shown below:

In the Claims

In column 26, line 29 (claim 1),

" $R(t) = A_2 e^{\alpha t} + B_2 e^{-\beta t}$ "

should read

-- $R(t) = A_2 e^{-\alpha t} + B_2 e^{-\beta t}$ --

Signed and Sealed this
Twenty-eighth Day of April, 2015

Michelle K. Lee
*Director of the United States Patent and Trademark Office*